US010183946B2

(12) United States Patent
Grether et al.

(10) Patent No.: US 10,183,946 B2
(45) Date of Patent: Jan. 22, 2019

(54) TRIAZOLO[4,5-D]PYRIMIDINES

(71) Applicant: Hoffmann—La Roche Inc., Little Falls, NJ (US)

(72) Inventors: Uwe Grether, Efringen-Kirchen (DE); Matthias Nettekoven, Grenzach-Wyhlen (DE); Mark Rogers-Evans, Bottmingen (CH); Sebastien Schmitt, Hagenthal-le-Bas (FR); Benjamin James Stenton, Cambridge (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/478,435

(22) Filed: Apr. 4, 2017

(65) Prior Publication Data
US 2017/0204103 A1  Jul. 20, 2017

Related U.S. Application Data

(63) Continuation of application No. PCT/EP2015/075654, filed on Nov. 4, 2015.

(30) Foreign Application Priority Data

Nov. 7, 2014  (EP) .................... 14192245

(51) Int. Cl.
*A61K 31/519* (2006.01)
*C07D 487/04* (2006.01)
(52) U.S. Cl.
CPC ................. *C07D 487/04* (2013.01)
(58) Field of Classification Search
CPC ................. A61K 31/519; C07D 487/04
USPC ....................... 514/261.1; 544/254
See application file for complete search history.

(56) References Cited

U.S. PATENT DOCUMENTS

| | | |
|---|---|---|
| 8,741,906 B2 | 6/2014 | Adam et al. |
| 9,056,866 B2 | 6/2015 | Adam et al. |
| 9,067,943 B2 | 6/2015 | Bissantz et al. |
| 9,593,123 B2 | 3/2017 | Grether et al. |

FOREIGN PATENT DOCUMENTS

| | | |
|---|---|---|
| WO | 2008/076810 A2 | 6/2008 |
| WO | 2009/059264 A1 | 5/2009 |
| WO | 2011/123372 A1 | 10/2011 |
| WO | 2013/068306 A1 | 5/2013 |
| WO | 2013/076182 A1 | 5/2013 |
| WO | 2015/032769 A1 | 3/2015 |
| WO | 2016/071375 A1 | 5/2016 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Akhmetshina et al., "The cannabinoid receptor CB2 exerts antifibrotic effects in experimental dermal fibrosis" Arthritis Rheum 60(4):1129-1136 ( 2009).
Ashton et al., "The cannabinoid CB2 receptor as a target for inflammation-dependent neurodegeneration" Current Neuropharmacol ((Abstract only)), 5:73-80 ( 2007).
Bab et al., "Cannabinoid receptors and the regulation of bone mass" Br J Pharmacol 153:182-188 ( 2008).
Bai et al., "MBC 94, a Conjugable Ligand for Cannabinoid CB2 Receptor Imaging," Bioconjugate Chemistry,vol. 19, No. 5, 2008, 988-992.
Batkai et al., "Cannabinoid-2 receptor mediates protection against hepatic ischemia/reperfusion injury" FASEB J 21:1788-1800 ( 2007).
Beltramo et al., "Cannabinoid type 2 receptor as a target for chronic-pain" Mini-Reviews in Medicinal Chemi 9:11-25 ( 2009).
Cabral et al., "Cannabinoid receptors in microglia of the central nervous system: immune functional relevance" J Leukocyte Biol 78:1192-1197 ( 2005).
Cabral et al., "Cb$_2$ receptors in the brain: role in central immune function" Br J Pharmacol 153:240-251 ( 2008).
Centonze et al., "The endocannabinoid system in peripheral lymphocytes as a mirror of neuroinflammatory diseases" Curr Pharmaceutcal Des 14:2370-2382 ( 2008).
International Preliminary Report on Patentability for International Patent Application No. PCT/EP2015/075654 dated Jan. 2, 2017.
Defer et al., "The cannabinoid receptor type 2 promotes cardiac myocyte and fibroblast survival and protects against ischemia/reperfusion-induced cardiomyopathy" FASEB J 23:2120-2130 ( 2009).
Feizi et al., "The preventive effect of cannabinoids on reperfusion-induced ischemia of mouse kidney" Experimental and Toxicologic Pathol 60:405-410 ( 2008).
Garcia-Gonzalez et al., "Cannabinoids inhibit fibrogenesis in diffuse systemic sclerosis fibroblasts" Rheumatology 48:1050-1056 ( 2009).
Julien et al., "Antifibrogenic role of the cannabinoid receptor CB2 in the liver" Gastroenterology 128:742-755 ( 2005).
Lotersztajn et al., "CB2 receptors as new therapeutic targets for liver diseases" Br J Pharmacol 153:286-289 ( 2008).
Lotersztajn et al., "Le systeme cannabinoide: perspectives therapeutiques au cours des hepatopathies chroniques" Gastroenterol Clin Biol 31:255-258 ( 2007).

(Continued)

Primary Examiner — Jeffrey H Murray
(74) Attorney, Agent, or Firm — Zong-Qiang Bill Tian

(57) ABSTRACT

The invention relates to a compound of formula (I)

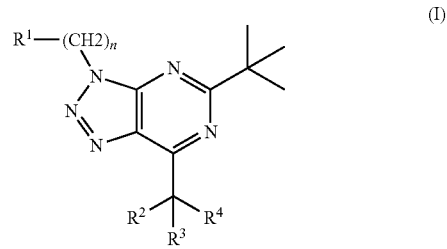

(I)

wherein $R^1$ to $R^4$ and n are defined as in the description and in the claims. The compound of formula (I) can be for treating.

18 Claims, No Drawings

(56) References Cited

OTHER PUBLICATIONS

Mach et al., "The role of the endocannabinoid system in atherosclerosis" J Neuroendocrinol 20( Suppl 1):53-57 ( 2008).

Mallat et al., "Cannabinoid receptors as new targets of antifibrosing strategies during chronic liver diseases" Expert Opin Ther Targets 11(3):403-409 ( 2007).

McAllister et al., "An Aromatic microdomain at the cannabinoid CB1 receptor constitutes anagonist/inverse agonist binding region," Journal of Medicinal Chemistry, vol. 46, No. 24, 2003, 5139-5152.

Miller et al., "$CB_2$ receptor-mediated migration of immune cells: it can go either way" Br J Pharmcol 153:299-308 ( 2008).

Munoz-Luque et al., "Regression of fibrosis after chronic stimulation of cannabinoid CB2 receptor in cirrhotic rats" J Pharmacol Exper Ther 324(2):475-483 ( 2008).

Pacher et al., "Endocannabinoids and cannabinoid receptors in ischaemia-reperfusion injury and preconditioning" Br J Pharmacol 153:252-262 ( 2008).

The English translation of the Colombian Office Action, dated Mar. 17, 2015, Application No. 14-067.070.

The English translation of the letter of opposition in the Costa Rican Application No. 2014-0136, which was notified by the Costa Rican Patent Office on Sep. 24, 2014.

Wright et al., "Cannabinoid $CB_2$ receptors in the gastrointestinal tract: a regulatory system in states of inflammation" Br J Pharmacol 153:263-270 ( 2008).

Yang et al., "Inhibition of hepatic tumour necrosis factor-$\alpha$ attenuates the anandamide-induced vasoconstrictive response in cirrhotic rat livers" Liver International 29(5):678-685 ( 2009).

Zhang et al., "Cannabinoid $CB_2$ receptor activation decreases cerebral infarction in a mouse focal ischemia/reperfusion model" J Cerebral Blood Flow Metab 27:1387-1396 ( 2007).

* cited by examiner

TRIAZOLO[4,5-D]PYRIMIDINES

CROSS REFERENCE TO RELATED APPLICATIONS

This application is a continuation of International Application No. PCT/EP2015/075654 having an International Filing Date of 4 Nov. 2015, the entire contents of which are incorporated herein by reference, and which claims the benefit of priority under 35 U.S.C. § 119 to EP 14192245.0 filed 7 Nov. 2014.

FIELD OF THE INVENTION

The present invention relates to organic compounds useful for therapy and/or prophylaxis in a mammal, and in particular to compounds that are preferential agonists of the Cannabinoid Receptor 2.

SUMMARY OF THE INVENTION

The invention relates in particular to a compound of formula (I)

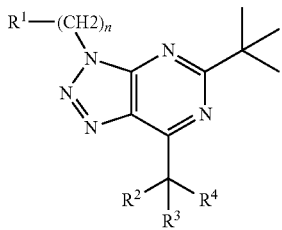

wherein
n is 0, 1 or 2;
$R^1$ is phenyl, halophenyl, alkyl sulfonylphenyl, alkyltetrazolyl, alkyloxadiazolyl, halohydroxyalkyl, oxolanyl, oxetanyl, haloalkyl, halopyridinyl or alkyloxetanyl;
$R^2$ is hydrogen, hydroxyl, halogen or haloalkyl; and
$R^3$ and $R^4$ are independently selected from alkyl; or
$R^3$ and $R^4$, together with the carbon atom to which they are attached, form cycloalkyl, thiethanyl, haloalkylcycloalkyl or oxothietanyl;
or
$R^2$ is absent; and
$R^3$ and $R^4$, together with the carbon atom to which they are attached, form alkylphenyl, halophenyl, alkoxyphenyl, halopyridinyl, alkylpyridinyl, alkylpyrazolyl, phenyl, alkyloxazolyl, pyrazolyl, imidazolyl, benzyltriazolyl or cycloalkenyl;
or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (FR) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the FR injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

Definitions

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl, isopropyl, butyl, isobutyl, tert.-butyl and pentyl. Methyl, ethyl, tert.-butyl and isobutyl are particular examples of "alkyl" in the compound of formula (I).

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl, cyclobutyl, cyclopentyl, cyclohexyl and cycloheptyl.

The term "cycloalkenyl", alone or in combination, refers to a cycloalkyl group as defined above wherein one or more carbon-carbon single bond is replaced by a carbon-carbon double bond. Examples of cycloalkenyl are cyclopentenyl, cyclohexenyl and cycloheptenyl. A preferred cycloalkenyl group is cyclopentenyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. A particular "alkoxy" is methoxy.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. Particular "halophenyl" are chlorophenyl and fluorophenyl and chlorofluorophenyl. Particular "haloalkyl" are trifluoropropyl, trifluorobutyl, difluoromethyl and fluoromethyl.

The terms "hydroxyl" and "hydroxy", alone or in combination, signify the —OH group.

The term "sulfonyl", alone or in combination, signifies the —SO$_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

DETAILED DESCRIPTION OF EMBODIMENTS

The invention relates in particular to:

A compound of formula (I) wherein $R^1$ is phenyl, halophenyl, alkyltetrazolyl or alkyloxadiazolyl;

A compound of formula (I) wherein $R^1$ is phenyl, chlorophenyl, methyltetrazolyl or methyloxadiazolyl;

A compound of formula (I) wherein $R^2$ is absent and $R^3$ and $R^4$, together with the carbon atom to which they are attached, form halopyridinyl, alkylpyrazolyl or alkyloxazolyl, or $R^2$ is hydroxyl and $R^3$ and $R^4$, together with the carbon atom to which they are attached, form cycloalkyl; A compound of formula (I) wherein $R^2$ is absent and $R^3$ and $R^4$, together with the carbon atom to which they are attached, form fluoropyridinyl, methylpyrazolyl or methyloxazolyl, or $R^2$ is hydroxyl and $R^3$ and $R^4$, together with the carbon atom to which they are attached, form cyclobutyl; and A compound of formula (I) wherein n is 1.

The invention further relates to a compound of formula (I) selected from 5-tert-butyl-3-[(2-chlorophenyl)methyl]-7-(4-methylphenyl)triazolo[4,5-d]pyrimidine;
5-tert-butyl-3-[(2-chlorophenyl)methyl]-7-(4-fluorophenyl)triazolo[4,5-d]pyrimidine;
5-tert-butyl-3-[(2-chlorophenyl)methyl]-7-(4-methoxyphenyl)triazolo[4,5-d]pyrimidine;
5-tert-butyl-3-[(2-chlorophenyl)methyl]-7-(2-fluorophenyl)triazolo[4,5-d]pyrimidine;
5-tert-butyl-7-(4-chloro-2-fluorophenyl)-3-[(2-chlorophenyl)methyl]triazolo[4,5-d]pyrimidine;
5-tert-butyl-3-[(2-chlorophenyl)methyl]-7-(6-fluoropyridin-3-yl)triazolo[4,5-d]pyrimidine;
5-tert-butyl-3-[(2-chlorophenyl)methyl]-7-(5-methylpyridin-2-yl)triazolo[4,5-d]pyrimidine;
5-tert-butyl-3-[(2-chlorophenyl)methyl]-7-(1-methylpyrazol-4-yl)triazolo[4,5-d]pyrimidine;
5-tert-butyl-3-[(2-chlorophenyl)methyl]-7-(2-methylpyrazol-3-yl)triazolo[4,5-d]pyrimidine;
5-tert-butyl-3-[(2-chlorophenyl)methyl]-7-phenyltriazolo[4,5-d]pyrimidine;
4-[5-tert-butyl-3-[(2-chlorophenyl)methyl]triazolo[4,5-d]pyrimidin-7-yl]-5-methyl-1,2-oxazole;
5-tert-butyl-7-(2-methylpyrazol-3-yl)-3-[(2-methylsulfonylphenyl)methyl]triazolo[4,5-d]pyrimidine;
5-tert-butyl-7-(2-methylpyrazol-3-yl)-3-[(1-methyltetrazol-5-yl)methyl]triazolo[4,5-d]pyrimidine;
3-[[5-tert-butyl-7-(2-methylpyrazol-3-yl)triazolo[4,5-d]pyrimidin-3-yl]methyl]-4-methyl-1,2,5-oxadiazole;
2-[[5-tert-butyl-7-(2-methylpyrazol-3-yl)triazolo[4,5-d]pyrimidin-3-yl]methyl]-5-methyl-1,3,4-oxadiazole;
1-[5-tert-butyl-7-(2-methylpyrazol-3-yl)triazolo[4,5-d]pyrimidin-3-yl]-4,4,4-trifluorobutan-2-ol;
(2S)-3-[5-tert-butyl-7-(2-methylpyrazol-3-yl)triazolo[4,5-d]pyrimidin-3-yl]-1,1,1-trifluoropropan-2-ol;
5-tert-butyl-7-(2-methylpyrazol-3-yl)-3-(oxolan-3-yl)triazolo[4,5-d]pyrimidine;
5-tert-butyl-7-(2-methylpyrazol-3-yl)-3-(oxetan-3-yl)triazolo[4,5-d]pyrimidine;
5-tert-butyl-7-(2-methylpyrazol-3-yl)-3-(3,3,3-trifluoropropyl)triazolo[4,5-d]pyrimidine;
5-tert-butyl-3-[(3-chloropyridin-2-yl)methyl]-7-(2-methylpyrazol-3-yl)triazolo[4,5-d]pyrimidine;
1-[5-tert-butyl-7-(2-methylpyrazol-3-yl)triazolo[4,5-d]pyrimidin-3-yl]-2-methylpropan-2-ol;
5-tert-butyl-3-[(3-methyl oxetan-3-yl)methyl]-7-(2-methylpyrazol-3-yl)triazolo[4,5-d]pyrimidine;
5-tert-butyl-7-(1-methylpyrazol-4-yl)-3-[(1-methyltetrazol-5-yl)methyl]triazolo[4,5-d]pyrimidine;
5-tert-butyl-3-[(1-methyltetrazol-5-yl)methyl]-7-(1H-pyrazol-4-yl)triazolo[4,5-d]pyrimidine;
5-tert-butyl-3-[(1-methyltetrazol-5-yl)methyl]-7-(1H-pyrazol-3-yl)triazolo[4,5-d]pyrimidine;
4-[5-tert-butyl-3-[(1-methyltetrazol-5-yl)methyl]triazolo[4,5-d]pyrimidin-7-yl]-5-methyl-1,2-oxazole;
5-tert-butyl-7-(1H-imidazol-2-yl)-3-[(1-methyltetrazol-5-yl)methyl]triazolo[4,5-d]pyrimidine;
7-(3-benzyltriazol-4-yl)-5-tert-butyl-3-[(1-methyltetrazol-5-yl)methyl]triazolo[4,5-d]pyrimidine;
3-[[5-tert-butyl-7-(6-fluoropyridin-3-yl)triazolo[4,5-d]pyrimidin-3-yl]methyl]-4-methyl-1,2,5-oxadiazole;
1-(3-benzyl-5-tert-butyltriazolo[4,5-d]pyrimidin-7-yl)cyclobutan-1-ol;
3-benzyl-5-tert-butyl-7-(1-fluorocyclobutyl)triazolo[4,5-d]pyrimidine;
1-[5-tert-butyl-3-[(2-chlorophenyl)methyl]triazolo[4,5-d]pyrimidin-7-yl]cyclobutan-1-ol;
1-[5-tert-butyl-3-[(2-chlorophenyl)methyl]triazolo[4,5-d]pyrimidin-7-yl]cyclopentan-1-ol;
1-[5-tert-butyl-3-[(2-chlorophenyl)methyl]triazolo[4,5-d]pyrimidin-7-yl]cyclohexan-1-ol;
1-[5-tert-butyl-3-[(2-chlorophenyl)methyl]triazolo[4,5-d]pyrimidin-7-yl]cycloheptan-1-ol;
1-[5-tert-butyl-3-[(2-chlorophenyl)methyl]triazolo[4,5-d]pyrimidin-7-yl]cyclooctan-1-ol;
3-[5-tert-butyl-3-[(2-chlorophenyl)methyl]triazolo[4,5-d]pyrimidin-7-yl]pentan-3-ol;
3-[5-tert-butyl-3-[(2-chlorophenyl)methyl]triazolo[4,5-d]pyrimidin-7-yl]thietan-3-ol;
1-[5-tert-butyl-3-[(2-chlorophenyl)methyl]triazolo[4,5-d]pyrimidin-7-yl]-3-(difluoromethyl)cyclobutan-1-ol;
1-[5-tert-butyl-3-[(2-chlorophenyl)methyl]triazolo[4,5-d]pyrimidin-7-yl]-3-(difluoromethyl)cyclobutan-1-ol;
3-[5-tert-butyl-3-[(2-chlorophenyl)methyl]triazolo[4,5-d]pyrimidin-7-yl]-1-oxothietan-3-ol;
5-tert-butyl-3-[(2-chlorophenyl)methyl]-7-[1-(fluoromethyl)cyclopropyl]triazolo[4,5-d]pyrimidine;
5-tert-butyl-3-[(2-chlorophenyl)methyl]-7-(cyclopenten-1-yl)triazolo[4,5-d]pyrimidine;
5-tert-butyl-3-[(2-chlorophenyl)methyl]-7-cyclopentyl-triazolo[4,5-d]pyrimidine; and
3-benzyl-5-tert-butyl-7-cyclopentyl-triazolo[4,5-d]pyrimidine.

The invention also relates to a compound of formula (I) selected from 5-tert-butyl-3-[(2-chlorophenyl)methyl]-7-(6-fluoropyridin-3-yl)triazolo[4,5-d]pyrimidine;
3-[[5-tert-butyl-7-(2-methylpyrazol-3-yl)triazolo[4,5-d]pyrimidin-3-yl]methyl]-4-methyl-1,2,5-oxadiazole;
4-[5-tert-butyl-3-[(1-methyltetrazol-5-yl)methyl]triazolo[4,5-d]pyrimidin-7-yl]-5-methyl-1,2-oxazole;
3-[[5-tert-butyl-7-(6-fluoropyridin-3-yl)triazolo[4,5-d]pyrimidin-3-yl]methyl]-4-methyl-1,2,5-oxadiazole; and
1-(3-benzyl-5-tert-butyltriazolo[4,5-d]pyrimidin-7-yl)cyclobutan-1-ol.

The preparation of the compound of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 2nd Edition, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

In the following description and schemes, n and $R^1$-$R^4$ have the meaning as defined above unless indicated otherwise.

In the present description the following abbreviations are used:

MS=mass spectrometry; ESI=electrospray; NMR=nuclear magnetic resonance; DBU=1,8-Diazabicyclo[5.4.0]undec-7-en; DCM=dichloromethane; DEAD=diethyl azodicarboxylate; DIAD=diisopropyl azodicarboxylate; DIPEA=diisopropylethyl amine; DMA=diemthylacetamide; DMF=dimethylformamide; DMSO=dimethyl-sulfoxide; HPLC=LC=high performance liquid chromatography; m-CPBA=meta-chloroperoxybenzoic acid; NMP=N-methylpyrrolidine; Ph=phenyl; PMB=para-methoxy benzyl; TFA=trifluoroacetic acid; THF=tetrahydrofuran; tlc=thin layer chromatography; CAN=CAS Registry Number.

The preparation of the compound of formula (I) may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 2nd Edition, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

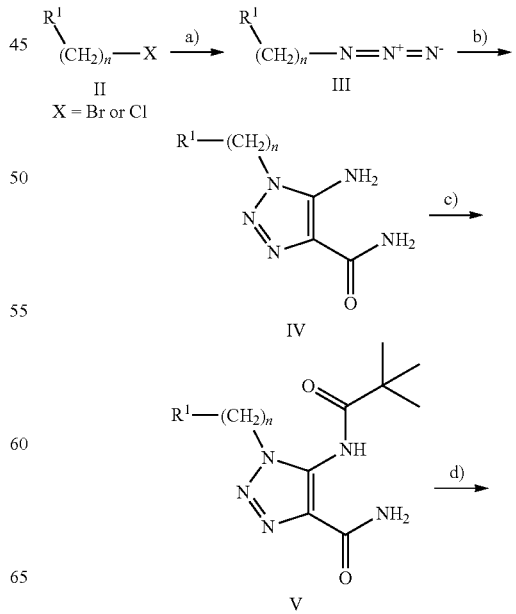

Scheme 1

-continued

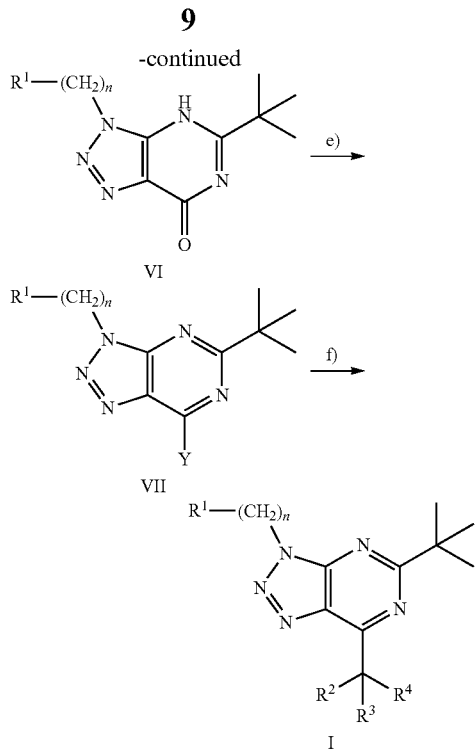

Y is chloride or bromide.

a) Halides II are either commercially available or can be synthesized according to methods known in the art. These halides II are conveniently reacted with sodium azide in a suitable solvent such as acetonitrile, ethanol or DMF to afford azide derivatives III. Alternative preferred conditions involve the use of solvents like DMA, NMP or DMSO, even more preferred are NMP and DMSO. In polar aprotic solvents like NMP and DMSO, the alkylations can usually be conducted at lower temperature than for example in acetonitrile, often at room temperature to 40° C. (this is the case for example for BnCl, 1-chloro-2-(chloromethyl)benzene or PMB-Cl; this depends of course on the reactivity of the halides II) and hence provide a better process safety window (caution organic azides are of course know to be potentially dangerous and process safety has always to be carefully assessed). The addition of water can be beneficial as it increases the solubility of sodium azide.

b) Triazole derivatives IV can be prepared by a [3+2] cycloaddition of azide derivatives III with 2-cyanoacetamide in the presence of an appropriate base such as sodium methoxide or sodium ethoxide in a suitable solvent such as methanol, ethanol or DMF. Alternative preferred conditions involve reacting the azide with 2-cyanoacetamide in solvents like NMP or DMSO, in the presence of sodium hydroxide.

c) Triazole IV can conveniently be reacted with an appropriate acid chloride (commercially available or known in the art) in the presence of a base (pyridine, DIPEA, NEt$_3$ and the like) in the presence or absence of a solvent (DCM, DMF and the like) to access triazole deivatives V.

d) Cyclisation of triazole V is can conveniently be done under basic conditions. It proved advantageous to perform this reaction under aqueous conditions in the presence of a base. Suitable bases are NaHCO$_3$ or KHCO$_3$ and the like. This gave access to triazolopyrimidine derivatives VI. These derivatives can be intermediate compounds, however preferably when R$^1$=substituted or unsubstituted phenyl group such as p-methoxy phenyl, and n is 1, these groups can be cleaved with TFA, CAN, hydrogenation and the like to access derivatives I. The benzyl group can be cleaved under standard hydrogenolysis conditions also for example in the presence of acids.

The triazole derivatives VI (R$^1$=H) is conveniently reacted either with a halide, a sulfonate or an epoxide in the presence of suitable base such as DIPEA, DBU, K$_2$CO$_3$, or Cs$_2$CO$_3$ in a solvent such as DMF, dioxane or toluene, or alternatively with an alcohol under Mitsunobu reaction conditions using suitable diazodicarboxylate (DEAD, DIAD and the like) and phosphine such as PBu$_3$ or PPh$_3$ in an appropriate solvent such as THF, DCM, toluene to afford intermediate triazolopyrimidine derivatives VI (wherein R$^1$≠H).

e) Chlorides VII can be obtained by reaction of VI with a chlorination reagent such as POCl$_3$, SOCl$_2$ or (COCl)$_2$ in the presence of an appropriate base such as N,N-diethyl aniline, lutidine, or pyridine. Alternative preferred conditions involve the use of the Vislmeier reagent as chlorinating agent. It can also be generated in situ by reacting oxalyl chloride with DMF. The chlorination can be performed for example in acetonitrile, DCM or AcOEt, preferably in DCM. These conditions allow for mild reaction temperature and for example, avoid the quench of excess POCl$_3$ upon work-up. The crude product can be used in the next step.

f) VII are conveniently reacted with various boronic acids or esters under palladium catalysis to yield triazolo-pyrimidine derivatives I.

These derivatives can be the final compounds, however preferably when R$^1$=substituted or unsubstituted phenyl group such as p-methoxy phenyl and n is 1, these groups can be cleaved with TFA, CAN, hydrogenation and the like to access derivatives I (R$^1$=H). The benzyl group can be cleaved under standard hydrogenolysis conditions also for example in the presence of acids.

The triazole derivatives I (R$^1$=H) is conveniently reacted either with a halide, a sulfonate or an epoxide in the presence of suitable base such as DIPEA, DBU, K$_2$CO$_3$, or Cs$_2$CO$_3$ in a solvent such as DMF, dioxane or toluene, or alternatively with an alcohol under Mitsunobu reaction conditions using suitable diazodicarboxylate (DEAD, DIAD and the like) and phosphine such as PBu$_3$ or PPh$_3$ in an appropriate solvent such as THF, DCM, toluene to afford final triazolopyrimidine derivatives I.

Chlorides or bromides VII can furthermore be subjected to a halogen metal exchange reaction, followed by the subsequent treatment with an electrophile to afford final compounds I using reaction conditions which are well known to a person skilled in the art. E.g. the halogen metal exchange can be accomplished using n-buthyllithium in THF at −78° C. Subsequent trapping with a ketone as electrophile preferably at −78° C. as well, provides final compounds I with R$^2$=OH.

The invention also relates to a process for the preparation of a compound of formula (I) comprising one of the following steps:

(a) the reaction of a compound of formula (II)

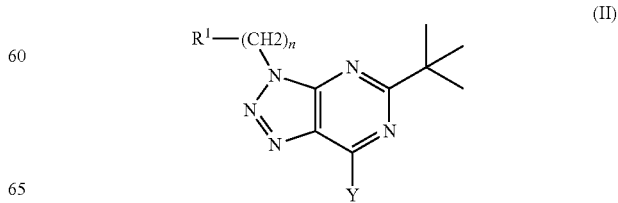

in the presence of $B(OH)_2CR^2R^3R^4$ or $B(OR)_2CR^2R^3R^4$ in the presence of a base and a palladium catalyst, wherein n and $R^1$ to $R^4$ are as defined above, Y is chloride or bromide and $B(OR)_2$ is 4,4,5,5-tetramethyl-1,3,2-dioxaborolanyl; or (b) the reaction of a compound of formula (II) as defined above in the presence of n-butyllithium followed by the addition of $R^3C(O)R^4$, wherein $R^3$ and $R^4$ are as defined above.

In step (a), the base is for example $CS_2CO_3$.

In step (a), the palladium catalyst is for example a catalyst typically used in Suzuki coupling, for example $Pd(PPh_3)_4$.

The invention also relates to a compound of formula (I) when manufactured according to a process of the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention also relates in particular to:

The use of a compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

A compound of formula (I) for use in the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis; and A method for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention will now be illustrated by the following examples which have no limiting character.

EXAMPLES

Example 1

5-tert-butyl-3-[(2-chlorophenyl)methyl]-7-(4-methylphenyl)triazolo[4,5-d]pyrimidine

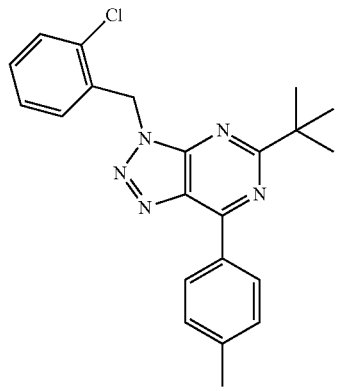 [SMILES: Cc1ccc(-c2nc(C(C)(C)C)nc3c2nnn3Cc2ccccc2Cl)cc1]

a) 5-Amino-1-(2-chlorobenzyl)-1H-1,2,3-triazole-4-carboxamide

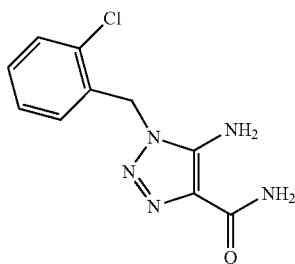 [SMILES: NC(=O)c1nnn(Cc2ccccc2Cl)c1N]

A mixture of 1-(bromomethyl)-2-chlorobenzene (5 g, 24.3 mmol) and sodium azide (2.37 g, 36.5 mmol) in acetonitrile (48.7 mL) was refluxed for 3 h under N₂ atmosphere. Then, the mixture was filtered and concentrated in vacuo. The residue was diluted in DCM, washed with H₂O and brine, dried over Na₂SO₄ and concentrated in vacuo to afford crude 1-(azidomethyl)-2-chlorobenzene. The residue was used for the next reaction without further purification.

A mixture of the above crude residue, 2-cyanoacetamide (1.82 g, 21.7 mmol) and sodium ethanolate (1.47 g, 21.7 mmol) in ethanol (43.3 mL) was refluxed for 3 h under N₂ atmosphere. The mixture was concentrated in vacuo, diluted with 4M AcOH aq. and filtered. The residue was washed with H₂O and dried in vacuo to afford 5-amino-1-(2-chlorobenzyl)-1H-1,2,3-triazole-4-carboxamide as pale-orange solid (5.10 g, 94% for 2 steps). MS(m/e): 252.1 (MH⁺).

b) 5-tert-Butyl-3-(2-chlorobenzyl)-3H-[1,2,3]triazolo[4,5-d]pyrimidin-7(4H)-one

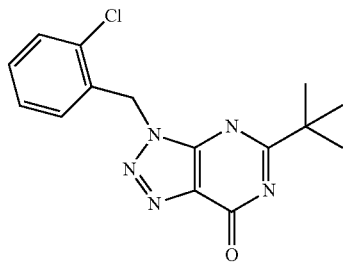 [SMILES: CC(C)(C)c1nc(=O)c2nnn(Cc3ccccc3Cl)c2[nH]1]

A mixture of 5-amino-1-(2-chlorobenzyl)-1H-1,2,3-triazole-4-carboxamide (2 g, 7.95 mmol) and pivaloyl chloride (1.47 mL, 11.9 mmol) in pyridine (3.98 mL) was stirred at 80° C. for 2 h under N₂ atmosphere. Then, to the reaction mixture was added 8M sodium hydroxide aq. (2.98 mL, 23.8 mmol) and methanol (3.98 mL). After being stirred at 80° C. for 2 h, the reaction mixture was poured into 1M HCl aq., extracted with diethyl ether, washed with 2M HCl, water and brine, dried over Na₂SO₄ and concentrated in vacuo to afford the mixture of crude 1-(2-chlorobenzyl)-5-pivalamido-1H-1,2,3-triazole-4-carboxamide and N-(1-(2-chlorobenzyl)-4-cyano-1H-1,2,3-triazol-5-yl)pivalamide. The residue was used for the next reaction without further purification.

A mixture of the above crude residue and KHCO₃ (3.00 g, 30.0 mmol) in H₂O (60.0 mL) was refluxed for 18 h. The reaction mixture was poured into 1M HCl aq., extracted with EtOAc, washed with brine, dried over Na₂SO₄ and concentrated in vacuo. The crude residue was purified by flash chromatography (silica gel, 10% to 70% EtOAc in heptane) to afford 5-tert-butyl-3-(2-chlorobenzyl)-3H-[1,2,3]triazolo[4,5-d]pyrimidin-7(4H)-one as white solid (1.03 g, 41% for 2 steps). MS(m/e): 318.2 (MH⁺).

c) 5-tert-butyl-7-chloro-3-(2-chlorobenzyl)-3H-[1,2,3]triazolo[4,5-d]pyrimidine

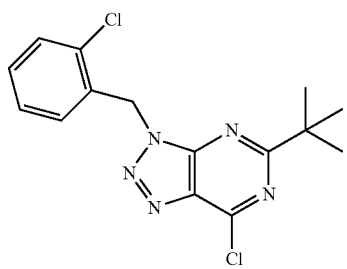 [SMILES: CC(C)(C)c1nc(Cl)c2nnn(Cc3ccccc3Cl)c2n1]

A mixture of 5-tert-butyl-3-(2-chlorobenzyl)-3H-[1,2,3]triazolo[4,5-d]pyrimidin-7(4H)-one (12.3 g, 38.7 mmol) and N,N-diethylaniline (12.3 mL, 77.4 mmol) in POCl₃ (252 mL, 2.73 mol) was refluxed for 2 h under N₂ atmosphere.

The reaction mixture was concentrated in vacuo, poured into ice and extracted with DCM (2×250 mL). The combined organic extracts were concentrated in vacuo and purified by column chromatography on silica eluting with a gradient formed from ethyl acetate and heptane to afford after evaporation of the product containing fractions 6.6 g (51%) of the title compound. MS(m/e): 336.2 (MK).

d) 5-tert-butyl-3-[(2-chlorophenyl)methyl]-7-(4-methylphenyl)triazolo[4,5-d]pyrimidine A mixture of 5-tert-butyl-7-chloro-3-(2-chlorobenzyl)-3H-[1,2,3]triazolo[4,5-d]pyrimidine (33.6 mg, 0.1 mmol), 1,1'-bis(diphenylphosphino)ferrocene-palladium(II)dichloride dichloromethane complex (0.7 mmol), $Cs_2CO_3$ (2M aq.) (150 µl, 0.3 mmol) and p-tolylboronic acid (20.4 mg, 0.15 mmol) in dioxane (2 mL) was heated to 100° C. for 2 h. The crude mixture was subjected to purification by preparative HPLC on reversed phase eluting with a gradient formed from acetonitrile, water and formic acid. Evaporation of the product containing fractions yielded the title compound (11 mg, 0.028 mmol, 28%). MS(m/e): 392.3 (MH$^+$).

Example 2

5-tert-butyl-3-[(2-chlorophenyl)methyl]-7-(4-fluorophenyl)triazolo[4,5-d]pyrimidine

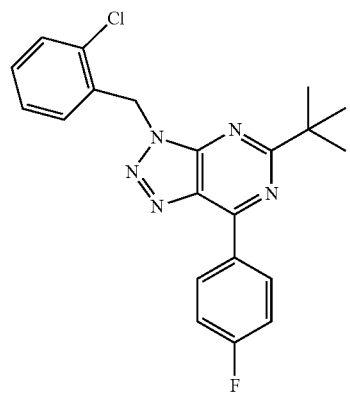 [SMILES: CC(C)(C)c1nc(-c2ccc(F)cc2)c2nnn(Cc3ccccc3Cl)c2n1]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 4-fluorophenylboronic acid. MS(m/e): 396.3 (MH$^+$).

Example 3

5-tert-butyl-3-[(2-chlorophenyl)methyl]-7-(4-methoxyphenyl)triazolo[4,5-d]pyrimidine

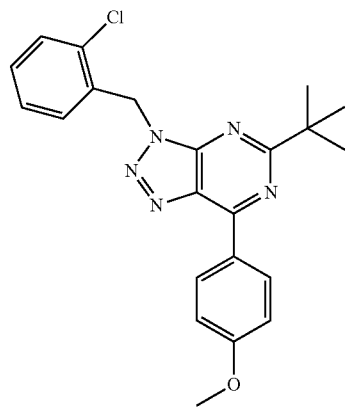 [SMILES: COc1ccc(-c2nc(C(C)(C)C)nc3c2nnn3Cc2ccccc2Cl)cc1]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 4-methoxyphenylboronic acid. MS(m/e): 408.3 (MH$^+$).

Example 4

5-tert-butyl-3-[(2-chlorophenyl)methyl]-7-(2-fluorophenyl)triazolo[4,5-d]pyrimidine

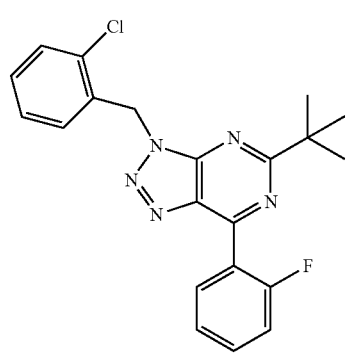 [SMILES: CC(C)(C)c1nc(-c2ccccc2F)c2nnn(Cc3ccccc3Cl)c2n1]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 2-fluorophenylboronic acid. MS(m/e): 396.3 (MH$^+$).

Example 5

5-tert-butyl-7-(4-chloro-2-fluorophenyl)-3-[(2-chlorophenyl)methyl]triazolo[4,5-d]pyrimidine

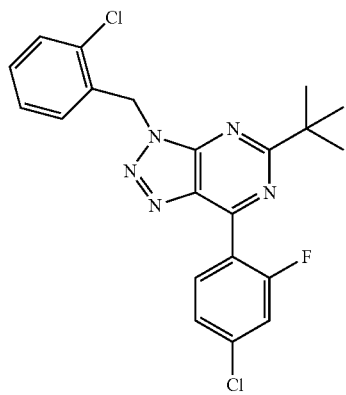 [SMILES: CC(C)(C)c1nc(-c2ccc(Cl)cc2F)c2nnn(Cc3ccccc3Cl)c2n1]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 4-chloro-2-fluorophenylboronic acid. MS(m/e): 430.3 (MH$^+$).

Example 6

5-tert-butyl-3-[(2-chlorophenyl)methyl]-7-(6-fluoropyridin-3-yl)triazolo[4,5-d]pyrimidine

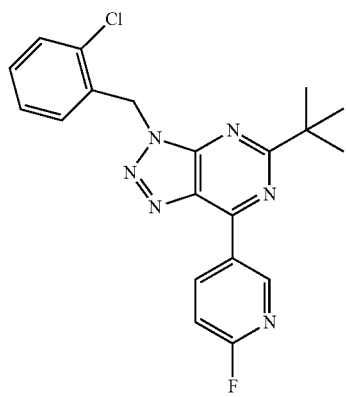 [SMILES: CC(C)(C)c1nc(-c2ccc(F)nc2)c2nnn(Cc3ccccc3Cl)c2n1]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 6-fluoropyridin-3-ylboronic acid. MS(m/e): 397.2 (MH$^+$).

Example 7

5-tert-butyl-3-[(2-chlorophenyl)methyl]-7-(5-methylpyridin-2-yl)triazolo[4,5-d]pyrimidine

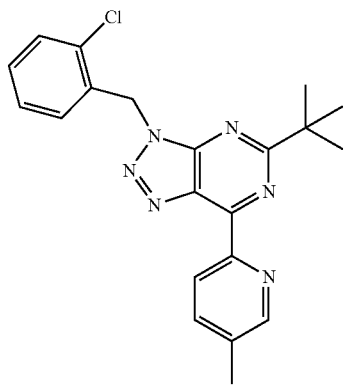 [SMILES: Cc1ccc(-c2nc(C(C)(C)C)nc3c2nnn3Cc2ccccc2Cl)nc1]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 5-methylpyridin-2-ylboronic acid. MS(m/e): 393.3 (MH$^+$).

Example 8

5-tert-butyl-3-[(2-chlorophenyl)methyl]-7-(1-methylpyrazol-4-yl)triazolo[4,5-d]pyrimidine

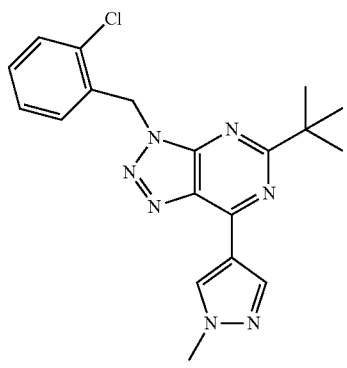 [SMILES: Cn1cc(-c2nc(C(C)(C)C)nc3c2nnn3Cc2ccccc2Cl)cn1]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 1-methyl-4-(4,4,5,5-tetramethyl-1,3,2-dioxaborolan-2-yl)-1H-pyrazole. MS(m/e): 382.2 (MH$^+$).

Example 9

5-tert-butyl-3-[(2-chlorophenyl)methyl]-7-(2-methylpyrazol-3-yl)triazolo[4,5-d]pyrimidine

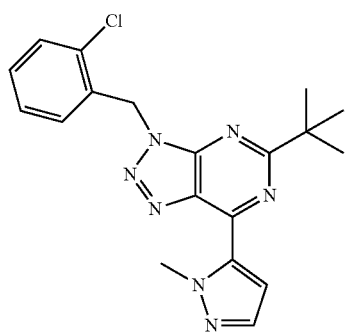 [SMILES: Cn1nccc1-c1nc(C(C)(C)C)nc2c1nnn2Cc1ccccc1Cl]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 1-methyl-5-(4,4,5,5-tetramethyl-1,3,2-dioxaborolan-2-yl)-1H-pyrazole. MS(m/e): 382.2 (MH$^+$).

Example 10

5-tert-butyl-3-[(2-chlorophenyl)methyl]-7-phenyltriazolo[4,5-d]pyrimidine

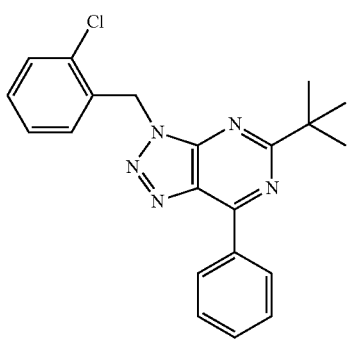 [SMILES: CC(C)(C)c1nc(-c2ccccc2)c2nnn(Cc3ccccc3Cl)c2n1]

A mixture of 5-tert-butyl-7-chloro-3-(2-chlorobenzyl)-3H-[1,2,3]triazolo[4,5-d]pyrimidine (20 mg, 0.059 mmol), tetrakis(triphenylphosphine)palladium(0) (6.87 mg, 0.059 mmol), sodium carbonate (12.6 mg, 0.12 mmol) and phenylboronic acid (10.9 mg, 0.089 mmol) in dioxane/water (2 mL/0.33 mL) was heated to 100° C. for 4 h. The crude mixture was subjected to purification by preparative HPLC on reversed phase eluting with a gradient formed from acetonitrile, water and formic acid. Evaporation of the product containing fractions yielded the title compound (3.6 mg, 16%). MS(m/e): 378.2 (MH$^+$).

Example 11

4-[5-tert-butyl-3-[(2-chlorophenyl)methyl]triazolo[4,5-d]pyrimidin-7-yl]-5-methyl-1,2-oxazole

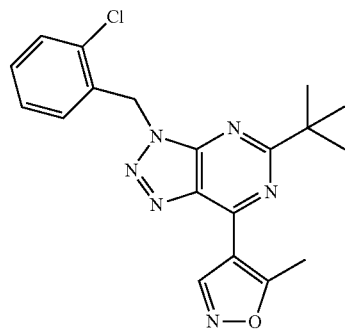 [SMILES: Cc1oncc1-c1nc(C(C)(C)C)nc2c1nnn2Cc1ccccc1Cl]

In analogy to the procedure described for the synthesis of 5-tert-butyl-3-[(2-chlorophenyl)methyl]-7-(4-methylphenyl)triazolo[4,5-d]pyrimidine (example 1) the title compound was prepared from 5-tert-butyl-7-chloro-3-(2-chlorobenzyl)-3H-[1,2,3]triazolo[4,5-d]pyrimidine and 5-methyl-4-(4,4,5,5-tetramethyl-1,3,2-dioxaborolan-2-yl)isoxazole. MS(m/e): 383.2 (MH$^+$).

Example 12

5-tert-butyl-7-(2-methylpyrazol-3-yl)-3-[(2-methylsulfonylphenyl)methyl]triazolo[4,5-d]pyrimidine

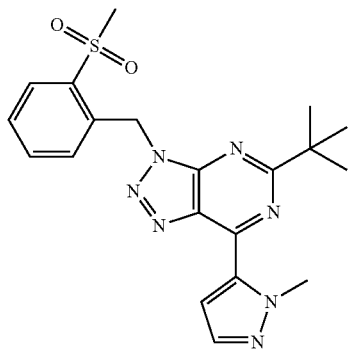 [SMILES: Cn1nccc1-c1nc(C(C)(C)C)nc2c1nnn2Cc1ccccc1S(C)(=O)=O]

a) 3-benzyl-5-tert-butyl-7-(1-methyl-1H-pyrazol-5-yl)-3H-[1,2,3]triazolo[4,5-d]pyrimidine

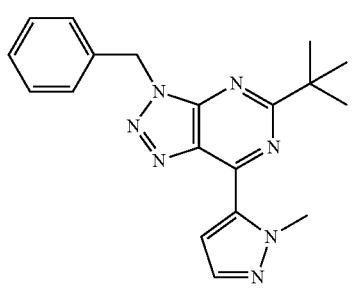 [SMILES: Cn1nccc1-c1nc(C(C)(C)C)nc2c1nnn2Cc1ccccc1]

In analogy to the procedure described for the synthesis of 5-tert-butyl-3-[(2-chlorophenyl)methyl]-7-(4-methylphenyl)triazolo[4,5-d]pyrimidine (example 1) the title compounds was prepared from 3-benzyl-5-tert-butyl-7-chloro-3H-[1,2,3]triazolo[4,5-d]pyrimidine (US 20130116236 A1) and 1-methyl-5-(4,4,5,5-tetramethyl-1,3,2-dioxaborolan-2-yl)-1H-pyrazole. MS(m/e): 348.2 (MH$^+$).

b) 5-tert-butyl-7-(2-methylpyrazol-3-yl)-3H-triazolo[4,5-d]pyrimidine

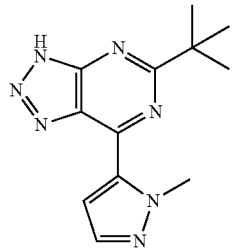 [SMILES: Cn1nccc1-c1nc(C(C)(C)C)nc2[nH]nnc12]

A solution of 3-benzyl-5-tert-butyl-7-(1-methyl-1H-pyrazol-5-yl)-3H-[1,2,3]triazolo[4,5-d]pyrimidine (5.55 g, 16 mmol) in 20 mL methanol was hydrogenated with H$_2$ (10 bar) over Pd/C 10% for 16 h at 100° C. The mixture was filtered and evaporated and the title compound was used in the consecutive step without further purification. MS(m/e): 299.2 (M+AcCN+H$^+$).

c) 5-tert-butyl-7-(2-methylpyrazol-3-yl)-3-[(2-methylsulfonylphenyl)methyl]triazolo[4,5-d]pyrimidine A mixture of 5-tert-butyl-7-(2-methylpyrazol-3-yl)-3H-triazolo[4,5-d]pyrimidine (56.1 mg, 0.22 mmol), 1-(bromomethyl)-2-(methylsulfonyl)benzene (70.6 mg, 0.28 mmol) and DBU (79.7 mg, 0.523 mmol) in DMF (3 mL) was stirred at room temperature for 4 h.
The crude mixture was subjected to purification by preparative HPLC on reversed phase eluting with a gradient formed from acetonitrile, water and formic acid. Evaporation of the product containing fractions yielded the title compound (2.8 mg, 3%). MS(m/e): 426.1 (MH$^+$).

Example 13

5-tert-butyl-7-(2-methylpyrazol-3-yl)-3-[(1-methyltetrazol-5-yl)methyl]triazolo[4,5-d]pyrimidine

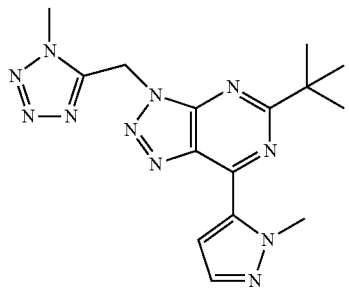 [SMILES: Cn1nccc1-c1nc(C(C)(C)C)nc2c1nnn2Cc1nnnn1C]

In analogy to the procedure described for the synthesis of 5-tert-butyl-7-(2-methylpyrazol-3-yl)-3-[(2-methylsulfonylphenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 5-(chloromethyl)-1-methyl-1H-tetrazole. MS(m/e): 354.1 (MH$^+$).

Example 14

3-[[5-tert-butyl-7-(2-methylpyrazol-3-yl)triazolo[4,5-d]pyrimidin-3-yl]methyl]-4-methyl-1,2,5-oxadiazole

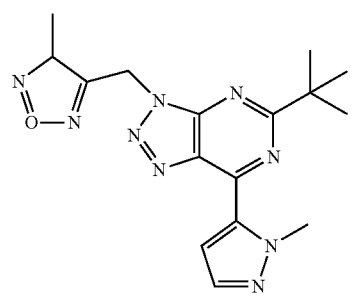

In analogy to the procedure described for the synthesis of 5-tert-butyl-7-(2-methylpyrazol-3-yl)-3-[(2-methyl sulfonylphenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 3-(bromomethyl)-4-methyl-1,2,5-oxadiazole. MS(m/e): 354.1 (MH$^+$).

Example 15

2-[[5-tert-butyl-7-(2-methylpyrazol-3-yl)triazolo[4,5-d]pyrimidin-3-yl]methyl]-5-methyl-1,3,4-oxadiazole

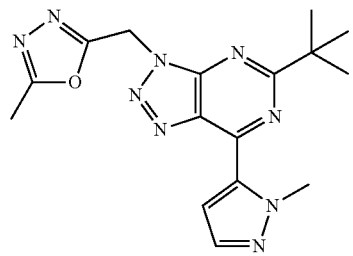 [SMILES: Cc1nnc(Cn2nnc3c(-c4ccnn4C)nc(C(C)(C)C)nc32)o1]

In analogy to the procedure described for the synthesis of 5-tert-butyl-7-(2-methylpyrazol-3-yl)-3-[(2-methylsulfonylphenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 2-(chloromethyl)-5-methyl-1,3,4-oxadiazole. MS(m/e): 354.1 (MH$^+$).

Example 16

1-[5-tert-butyl-7-(2-methylpyrazol-3-yl)triazolo[4,5-d]pyrimidin-3-yl]-4,4,4-trifluorobutan-2-ol

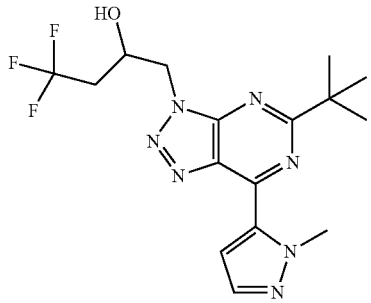 [SMILES: Cn1nccc1-c1nc(C(C)(C)C)nc2c1nnn2CC(O)CC(F)(F)F]

In analogy to the procedure described for the synthesis of 5-tert-butyl-7-(2-methylpyrazol-3-yl)-3-[(2-methylsulfonyl-phenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 2-(2,2,2-trifluoroethyl)oxirane. MS(m/e): 384.1 (MH$^+$).

Example 17

(2S)-3-[5-tert-butyl-7-(2-methylpyrazol-3-yl)triazolo[4,5-d]pyrimidin-3-yl]-1,1,1-trifluoropropan-2-ol

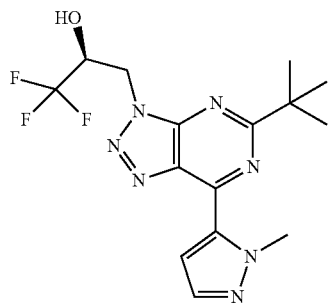 [SMILES: Cn1nccc1-c1nc(C(C)(C)C)nc2c1nnn2C[C@H](O)C(F)(F)F]

In analogy to the procedure described for the synthesis of 5-tert-butyl-7-(2-methylpyrazol-3-yl)-3-[(2-methylsulfonyl-phenyl)methyl]triazolo[4,5-d]pyrimidine (example 12) the title compound was prepared from 5-tert-butyl-7-(2-methylpyrazol-3-yl)-3H-triazolo[4,5-d]pyrimidine and (S)-2-(trifluoromethyl)oxirane. MS(m/e): 370.1 (MH$^+$).

Example 18

5-tert-butyl-7-(2-methylpyrazol-3-yl)-3-(oxolan-3-yl)triazolo[4,5-d]pyrimidine

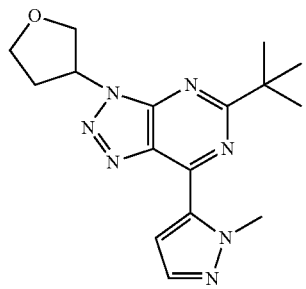 [SMILES: Cn1nccc1-c1nc(C(C)(C)C)nc2c1nnn2C1CCOC1]

In analogy to the procedure described for the synthesis of 5-tert-butyl-7-(2-methylpyrazol-3-yl)-3-[(2-methylsulfonyl-phenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 3-bromo-tetrahydrofuran. MS(m/e): 328.1 (MH$^+$).

Example 19

5-tert-butyl-7-(2-methylpyrazol-3-yl)-3-(oxetan-3-yl)triazolo[4,5-d]pyrimidine

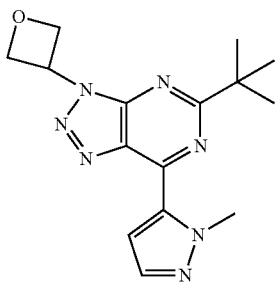 [SMILES: Cn1nccc1-c1nc(C(C)(C)C)nc2c1nnn2C1COC1]

In analogy to the procedure described for the synthesis of 5-tert-butyl-7-(2-methylpyrazol-3-yl)-3-[(2-methylsulfonyl-phenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 3-bromooxetane. MS(m/e): 314.1 (MH$^+$).

Example 20

5-tert-butyl-7-(2-methylpyrazol-3-yl)-3-(3,3,3-trifluoropropyl)triazolo[4,5-d]pyrimidine

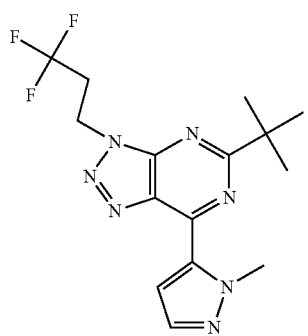 [SMILES: Cn1nccc1-c1nc(C(C)(C)C)nc2c1nnn2CCC(F)(F)F]

In analogy to the procedure described for the synthesis of 5-tert-butyl-7-(2-methylpyrazol-3-yl)-3-[(2-methylsulfonyl-phenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 3-bromo-1,1,1-trifluoropropane. MS(m/e): 314.1 (MH$^+$).

Example 21

5-tert-butyl-3-[(3-chloropyridin-2-yl)methyl]-7-(2-methylpyrazol-3-yl)triazolo[4,5-d]pyrimidine

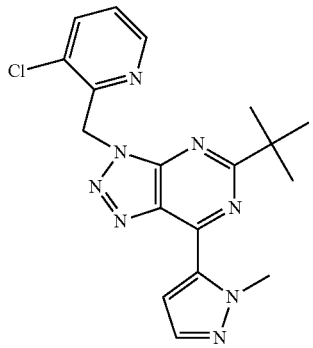 [SMILES: Cn1nccc1-c1nc(C(C)(C)C)nc2c1nnn2Cc1ncccc1Cl]

In analogy to the procedure described for the synthesis of 5-tert-butyl-7-(2-methylpyrazol-3-yl)-3-[(2-methylsulfonyl-phenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 3-chloro-2-(chloromethyl)pyridine. MS(m/e): 383.1 (MH$^+$).

Example 22

1-[5-tert-butyl-7-(2-methylpyrazol-3-yl)triazolo[4,5-d]pyrimidin-3-yl]-2-methylpropan-2-ol

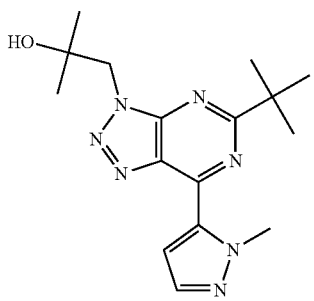 [SMILES: Cn1nccc1-c1nc(C(C)(C)C)nc2c1nnn2CC(C)(C)O]

In analogy to the procedure described for the synthesis of 5-tert-butyl-7-(2-methylpyrazol-3-yl)-3-[(2-methylsulfonyl-phenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 2,2-dimethyloxirane. MS(m/e): 330.2 (MH$^+$).

Example 23

5-tert-butyl-3-[(3-methyloxetan-3-yl)methyl]-7-(2-methylpyrazol-3-yl)triazolo[4,5-d]pyrimidine

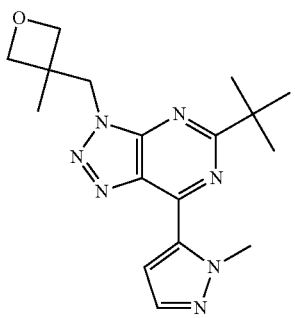 [SMILES: Cn1nccc1-c1nc(C(C)(C)C)nc2c1nnn2CC1(C)COC1]

In analogy to the procedure described for the synthesis of 5-tert-butyl-7-(2-methylpyrazol-3-yl)-3-[(2-methylsulfonyl-phenyl)methyl]triazolo[4,5-d]pyrimidine (example 12) the title compound was prepared from 5-tert-butyl-7-(2-methylpyrazol-3-yl)-3H-triazolo[4,5-d]pyrimidine and 3-(bromomethyl)-3-methyloxetane. MS(m/e): 342.2 (MH$^+$).

Example 24

5-tert-butyl-7-(1-methylpyrazol-4-yl)-3-[(1-methyltetrazol-5-yl)methyl]triazolo[4,5-d]pyrimidine

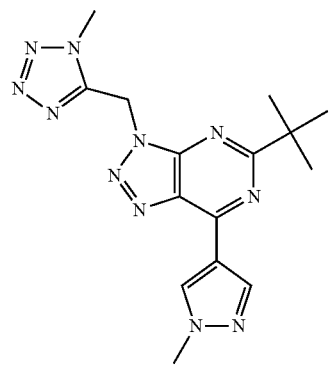 [SMILES: Cn1cc(-c2nc(C(C)(C)C)nc3c2nnn3Cc2nnnn2C)cn1]

a) 5-tert-butyl-3,4-dihydrotriazolo[4,5-d]pyrimidin-7-one

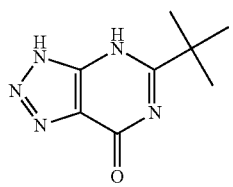

A solution of 3-benzyl-5-tert-butyl-triazolo[4,5-d]pyrimidin-7-ol (US 20130116236) (7.47 g, 26.4 mmol) in 100 mL methanol was hydrogenated with H$_2$ (10 bar) over Pd/C 10% for 20 h at 100° C. The mixture was filtered and evaporated and the title compound was used in the consecutive step without further purification. MS(m/e): 235.1 (M+AcCN+H⁺).

b) 5-tert-butyl-3-[(1-methyltetrazol-5-yl)methyl]-4H-triazolo[4,5-d]pyrimidin-7-one and 5-tert-butyl-2-[(1-methyltetrazol-5-yl)methyl]-4H-triazolo[4,5-d]pyrimidin-7-one

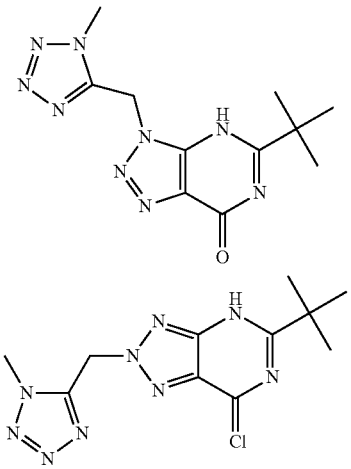

A mixture of 5-tert-butyl-3,4-dihydrotriazolo[4,5-d]pyrimidin-7-one (2.5 g, 12.3 mmol), 5-(chloromethyl)-1-methyl-1H-tetrazole (2.94 g, 22.2 mmol) and DBU (4.1 g, 27.1 mmol) in DMF (12 mL) was stirred over night at room temperature. The reaction mixture was poured into 1 M HCl (20 mL) and extracted with DCM (2×150 mL). The combined organic layers were dried over MgSO₄, adsorbed on isolute and purified by flash chromatography on silica eluting with a gradient formed from ethyl acetate and heptane.

Evaporation of product containing fractions yielded the title compounds 5-tert-butyl-2-((1-methyl-1H-tetrazol-5-yl)methyl)-2H-[1,2,3]triazolo[4,5-d]pyrimidin-7(4H)-one compound and 5-tert-butyl-3-((1-methyl-1H-tetrazol-5-yl)methyl)-3H-[1,2,3]triazolo[4,5-d]pyrimidin-7(4H)-one (1:1) (2.92 g, 5.05 mmol, 41%). MS(m/e): 290.1 (MK).

c) 5-tert-butyl-7-chloro-3-[(1-methyltetrazol-5-yl)methyl]triazolo[4,5-d]pyrimidine and 5-tert-butyl-7-chloro-2-[(1-methyltetrazol-5-yl)methyl]triazolo[4,5-d]pyrimidine

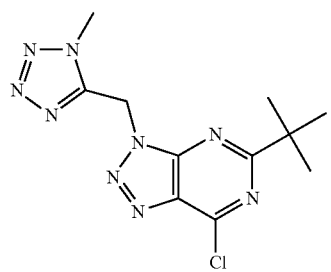

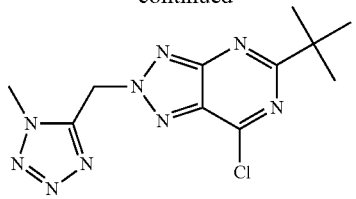

A mixture of 5-tert-butyl-3-[(1-methyltetrazol-5-yl)methyl]-4H-triazolo[4,5-d]pyrimidin-7-one and 5-tert-butyl-2-[(1-methyltetrazol-5-yl)methyl]-4H-triazolo[4,5-d]pyrimidin-7-one (2.92 g, 5.05 mmol) in DCM (100 mL) was treated with DMF (1.02 mL) and oxalyl chloride (1.28 g, 10.1 mmol) and stirred for 4 h at 22° C. The mixture was poured into 1M NaHCO₃ aq. (200 mL) and extracted with DCM (2×150 mL). The combined organic layers were dried with MgSO₄, evaporated and used in the consecutive step without further purification.

d) 5-tert-butyl-7-(1-methylpyrazol-4-yl)-3-[(1-methyltetrazol-5-yl)methyl]triazolo[4,5-d]pyrimidine A mixture of 5-tert-butyl-7-chloro-3-[(1-methyltetrazol-5-yl)methyl]triazolo[4,5-d]pyrimidine and 5-tert-butyl-7-chloro-2-[(1-methyltetrazol-5-yl)methyl]triazolo[4,5-d]pyrimidine (31.7 mg, 0.1 mmol), 1,1'-bis(diphenylphosphino)ferrocene-palladium(II)dichloride dichloromethane complex (5.72 mg, 0.07 mmol), Cs₂CO₃ (58.6 mg, 0.018 mmol) and 1-methyl-4-(4,4,5,5-tetramethyl-1,3,2-dioxaborolan-2-yl)-1H-pyrazole (27 mg, 0.13 mmol) in dioxane (2 mL) and water (0.1 mL) was stirred at 100° C. for 16 h. The crude mixture was subjected to purification by preparative HPLC on reversed phase eluting with a gradient formed from acetonitrile, water and formic acid. Evaporation of the product containing fractions yielded the title compound (7.4 mg, 21%). MS(m/e): 354.3 (MH⁺).

Example 25

5-tert-butyl-3-[(1-methyltetrazol-5-yl)methyl]-7-(1H-pyrazol-4-yl)triazolo[4,5-d]pyrimidine

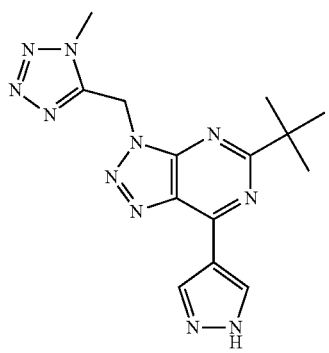 [SMILES: Cn1nnnc1Cn1nnc2c(-c3cn[nH]c3)nc(C(C)(C)C)nc21]

In analogy to the procedure described for the synthesis of 5-tert-butyl-7-(1-methylpyrazol-4-yl)-3-[(1-methyltetrazol-5-yl)methyl]triazolo[4,5-d]pyrimidine (example 24) the title compound was prepared from the mixture of 5-tert-butyl-7-chloro-3-[(1-methyltetrazol-5-yl)methyl]triazolo[4,5-d]

pyrimidine and 5-tert-butyl-7-chloro-2-[(1-methyltetrazol-5-yl)methyl]triazolo[4,5-d]pyrimidine (example 24, c) and 1H-pyrazol-4-ylboronic acid. MS(m/e): 340.3 (MH⁺).

Example 26

5-tert-butyl-3-[(1-methyltetrazol-5-yl)methyl]-7-(1H-pyrazol-3-yl)triazolo[4,5-d]pyrimidine

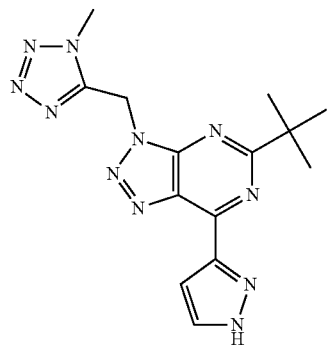 [SMILES: Cn1nnnc1Cn1nnc2c(-c3cc[nH]n3)nc(C(C)(C)C)nc21]

In analogy to the procedure described for the synthesis of 5-tert-butyl-7-(1-methylpyrazol-4-yl)-3-[(1-methyltetrazol-5-yl)methyl]triazolo[4,5-d]pyrimidine (example 24) the title compound was prepared from the mixture of 5-tert-butyl-7-chloro-3-[(1-methyltetrazol-5-yl)methyl]triazolo[4,5-d]pyrimidine and 5-tert-butyl-7-chloro-2-[(1-methyltetrazol-5-yl)methyl]triazolo[4,5-d]pyrimidine (example 24, c) and 3-(4,4,5,5-tetramethyl-1,3,2-dioxaborolan-2-yl)-1H-pyrazole. MS(m/e): 340.3 (MH⁺).

Example 27

4-[5-tert-butyl-3-[(1-methyltetrazol-5-yl)methyl]triazolo[4,5-d]pyrimidin-7-yl]-5-methyl-1,2-oxazole

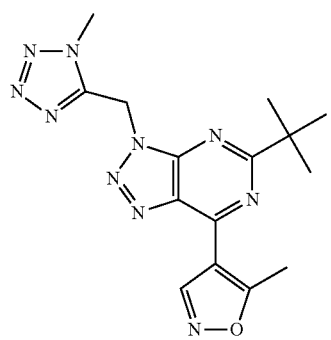 [SMILES: Cc1oncc1-c1nc(C(C)(C)C)nc2c1nnn2Cc1nnnn1C]

In analogy to the procedure described for the synthesis of 5-tert-butyl-7-(1-methylpyrazol-4-yl)-3-[(1-methyltetrazol-5-yl)methyl]triazolo[4,5-d]pyrimidine (example 24) the title compound was prepared from the mixture of 5-tert-butyl-7-chloro-3-[(1-methyltetrazol-5-yl)methyl]triazolo[4,5-d]pyrimidine and 5-tert-butyl-7-chloro-2-[(1-methyltetrazol-5-yl)methyl]triazolo[4,5-d]pyrimidine (example 24, c) and 5-methyl-4-(4,4,5,5-tetramethyl-1,3,2-dioxaborolan-2-yl)isoxazole. MS(m/e): 355.3 (MH⁺).

Example 28

5-tert-butyl-7-(1H-imidazol-2-yl)-3-[(1-methyltetrazol-5-yl)methyl]triazolo[4,5-d]pyrimidine

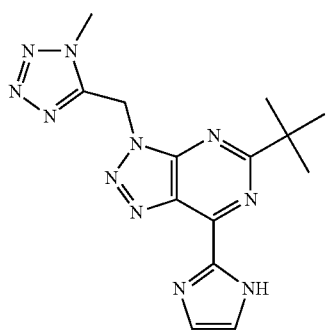 [SMILES: Cn1nnnc1Cn1nnc2c(-c3ncc[nH]3)nc(C(C)(C)C)nc21]

In analogy to the procedure described for the synthesis of 5-tert-butyl-7-(1-methylpyrazol-4-yl)-3-[(1-methyltetrazol-5-yl)methyl]triazolo[4,5-d]pyrimidine (example 24) the title compound was prepared from the mixture of 5-tert-butyl-7-chloro-3-[(1-methyltetrazol-5-yl)methyl]triazolo[4,5-d]pyrimidine and 5-tert-butyl-7-chloro-2-[(1-methyltetrazol-5-yl)methyl]triazolo[4,5-d]pyrimidine (example 24, c) and 1H-imidazol-2-ylboronic acid hydrochloride. MS(m/e): 340.3 (MH⁺).

Example 29

7-(3-benzyltriazol-4-yl)-5-tert-butyl-3-[(1-methyltetrazol-5-yl)methyl]triazolo[4,5-d]pyrimidine

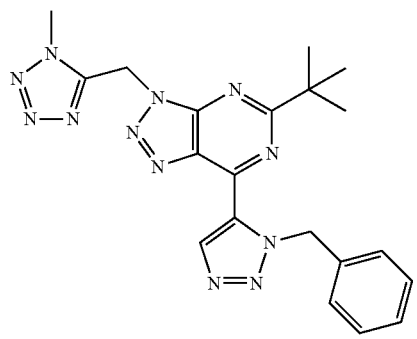 [SMILES: Cn1nnnc1Cn1nnc2c(-c3cnnn3Cc3ccccc3)nc(C(C)(C)C)nc21]

a) 2-[5-tert-butyl-3-[(1-methyltetrazol-5-yl)methyl]triazolo[4,5-d]pyrimidin-7-yl]ethynyl-trimethyl-silane and 2-[5-tert-butyl-2-[(1-methyltetrazol-5-yl)methyl]triazolo[4,5-d]pyrimidin-7-yl]ethynyl-trimethyl-silane

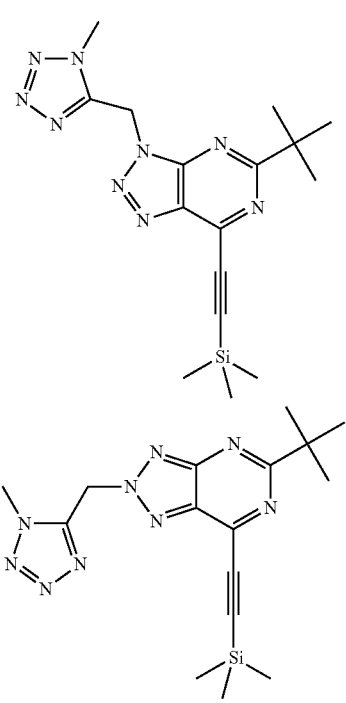

A mixture of 5-tert-butyl-7-chloro-3-[(1-methyltetrazol-5-yl)methyl]triazolo[4,5-d]pyrimidine and 5-tert-butyl-7-chloro-2-[(1-methyltetrazol-5-yl)methyl]triazolo[4,5-d]pyrimidine (2.2 g, 6.1 mmol), ethynyltrimethylsilane (1.1 g, 1.58 mL, 10.9 mmol), triethylamine (1.23 g, 1.69 ml, 12.2 mmol), copper (I) iodide (116 mg, 608 μmol) and bis(triphenylphosphine)palladium (II) chloride (218 mg, 304 mmol) in dioxane (30 mL) was degased and flushed with argon. The mixture was stirred for 1 h at room temperature, adsorbed on isolute and purified by flash chromatography on silica eluting with a gradient formed from ethyl acetate and heptane to yield after evaporation of the product containing fractions 1.65 g (73%) of the title compounds. MS(m/e): 370.3 (MH$^+$).

b) 7-(3-benzyltriazol-4-yl)-5-tert-butyl-3-[(1-methyltetrazol-5-yl)methyl]triazolo[4,5-d]pyrimidine A mixture of 2-[5-tert-butyl-3-[(1-methyltetrazol-5-yl)methyl]triazolo[4,5-d]pyrimidin-7-yl]ethynyl-trimethyl-silane and 2-[5-tert-butyl-2-[(1-methyltetrazol-5-yl)methyl]triazolo[4,5-d]pyrimidin-7-yl]ethynyl-trimethyl-silane (881 mg, 2.38 mmol) and 1M TBAF in THF (4.77 ml, 4.77 mmol) in MeOH (10 mL) was stirred for 1 h at room temperature. (Azidomethyl)benzene (381 mg, 358 μl, 2.86 mmol) and copper (I) iodid (454 mg, 2.38 mmol) were added and the mixture was stirred for 30 min at room temperature. The crude mixture was purified by flash chromatography on silica eluting with a gradient formed from ethyl acetate and heptane to yield after evaporation of the product containing fractions 272 mg (27%) of the title compounds. MS(m/e): 431.3 (MH$^+$).

Example 30

3-[[5-tert-butyl-7-(6-fluoropyridin-3-yl)triazolo[4,5-d]pyrimidin-3-yl]methyl]-4-methyl-1,2,5-oxadiazole

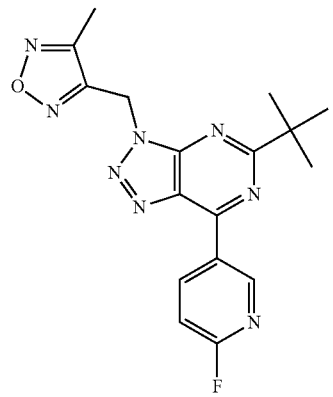 [SMILES: Cc1nonc1Cn1nnc2c(-c3ccc(F)nc3)nc(C(C)(C)C)nc21]

a) 5-tert-butyl-3-[(4-methyl-1,2,5-oxadiazol-3-yl)methyl]-6H-triazolo[4,5-d]pyrimidin-7-one and 5-tert-butyl-2-[(4-methyl-1,2,5-oxadiazol-3-yl)methyl]-6H-triazolo[4,5-d]pyrimidin-7-one and 5-tert-butyl-1-[(4-methyl-1,2,5-oxadiazol-3-yl)methyl]-6H-triazolo[4,5-d]pyrimidin-7-one

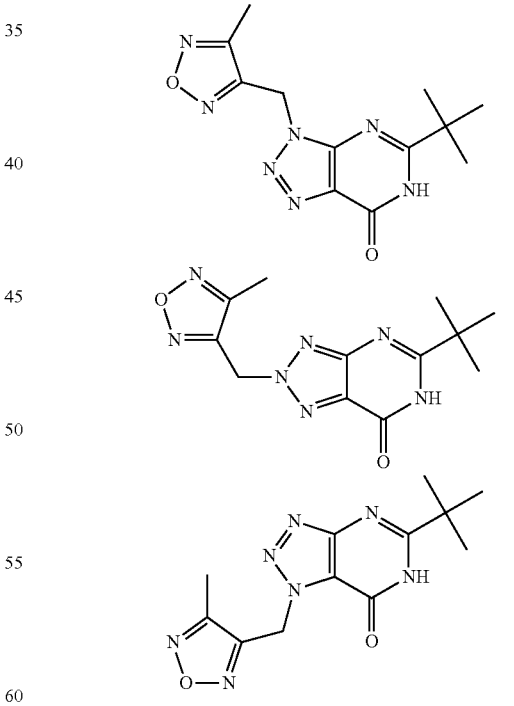

In analogy to the procedure described for the synthesis of 5-tert-butyl-3-[(1-methyltetrazol-5-yl)methyl]-4H-triazolo[4,5-d]pyrimidin-7-one and 5-tert-butyl-2-[(1-methyltetrazol-5-yl)methyl]-4H-triazolo[4,5-d]pyrimidin-7-one (example 24, b) the title compounds were prepared from 5-tert-butyl-3,4-dihydrotriazolo[4,5-d]pyrimidin-7-one and 3-(bromomethyl)-4-methyl-1,2,5-oxadiazole and utilized in the subsequent step without further purification.

b) 3-[(5-tert-butyl-7-chloro-triazolo[4,5-d]pyrimidin-3-yl)methyl]-4-methyl-1,2,5-oxadiazole and 3-[(5-tert-butyl-7-chloro-triazolo[4,5-d]pyrimidin-2-yl)methyl]-4-methyl-1,2,5-oxadiazole and 3-[(5-tert-butyl-7-chloro-triazolo[4,5-d]pyrimidin-1-yl)methyl]-4-methyl-1,2,5-oxadiazole

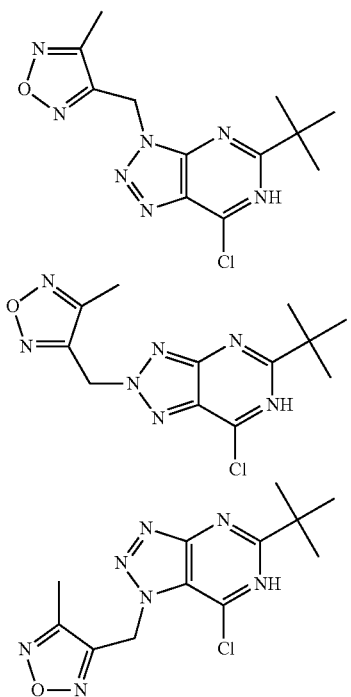

In analogy to the procedure described for the synthesis of 5-tert-butyl-7-chloro-3-[(1-methyltetrazol-5-yl)methyl]triazolo[4,5-d]pyrimidine and 5-tert-butyl-7-chloro-2-[(1-methyltetrazol-5-yl)methyl]triazolo[4,5-d]pyrimidine (example 24, b) the title compounds were prepared from 5-tert-butyl-3-[(4-methyl-1,2,5-oxadiazol-3-yl)methyl]-6H-triazolo[4,5-d]pyrimidin-7-one and 5-tert-butyl-2-[(4-methyl-1,2,5-oxadiazol-3-yl)methyl]-6H-triazolo[4,5-d]pyrimidin-7-one and 5-tert-butyl-1-[(4-methyl-1,2,5-oxadiazol-3-yl)methyl]-6H-triazolo[4,5-d]pyrimidin-7-one and oxalyl chloride. The mixture was used crude in the consecutive step.

c) 3-[[5-tert-butyl-7-(6-fluoropyridin-3-yl)triazolo[4,5-d]pyrimidin-3-yl]methyl]-4-methyl-1,2,5-oxadiazole In analogy to the procedure described for the synthesis of 5-tert-butyl-7-(1-methylpyrazol-4-yl)-3-[(1-methyltetrazol-5-yl)methyl]triazolo[4,5-d]pyrimidine (example 24) the title compound was prepared from the mixture of 3-[(5-tert-butyl-7-chloro-triazolo[4,5-d]pyrimidin-3-yl)methyl]-4-methyl-1,2,5-oxadiazole and 3-[(5-tert-butyl-7-chloro-triazolo[4,5-d]pyrimidin-2-yl)methyl]-4-methyl-1,2,5-oxadiazole and 3-[(5-tert-butyl-7-chloro-triazolo[4,5-d]pyrimidin-1-yl)methyl]-4-methyl-1,2,5-oxadiazole and 1H-imidazol-2-ylboronic acid hydrochloride. MS(m/e): 368.1 (MH$^+$).

Example 31

1-(3-Benzyl-5-tert-butyltriazolo[4,5-d]pyrimidin-7-yl)cyclobutan-1-ol

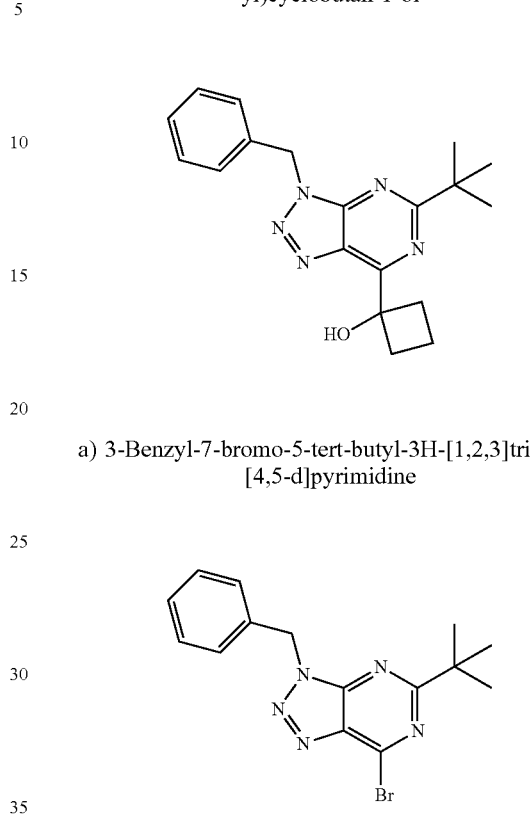

a) 3-Benzyl-7-bromo-5-tert-butyl-3H-[1,2,3]triazolo[4,5-d]pyrimidine

A mixture of 3-benzyl-5-tert-butyl-3H-[1,2,3]triazolo[4,5-d]pyrimidin-7(4H)-one (2 g, 7.06 mmol; CAN 1433363-42-8), K$_2$CO$_3$ (2.93 g, 21.2 mmol) and phosphoryl tribromide (6.07 g, 21.2 mmol) in acetonitrile (70 mL) was heated to reflux for 19 h, poured slowly onto 50 mL sat. NaHCO$_3$/ice and extracted with DCM (2×50 mL). The combined organic layers were washed with icewater/brine (50 mL), dried over Na$_2$SO$_4$, filtered and concentrated in vacuo to give a brown solid which was purified by flash chromatography (silica gel, 50 g, 0% to 5% EtOAc in heptane) to give the title compound (1.99 g, 81%) as white solid. MS(m/e): 346.4 (MH$^+$).

b) 1-(3-Benzyl-5-tert-butyltriazolo[4,5-d]pyrimidin-7-yl)cyclobutan-1-ol

A mixture of mol-sieve, 3-benzyl-7-bromo-5-tert-butyl-3H-[1,2,3]triazolo[4,5-d]pyrimidine (647 mg, 1.87 mmol) and cyclobutanone (144 mg, 154 µL, 2.06 mmol) in dry THF (7.5 mL) was stirred under an argon atmosphere at RT for 10 minutes and then cooled to −78° C. n-Butyllithium (1.4 mL, 2.24 mmol) was added with a syringe over 20 min. The mixture was stirred at −78° C. for 3 h, quenched with water (2 mL), left to warm to RT, poured onto sat. NH$_4$Cl solution and extracted with EtOAc (2×20 mL). The combined organic layers were washed with icewater/brine, dried over Na$_2$SO$_4$ and concentrated in vacuo to give 727 mg of a yellow oil which was purified by preparative HPLC to yield 197 mg (31%) of the title compound as light yellow oil. MS(m/e): 338.2 (MH$^+$).

Example 32

3-Benzyl-5-tert-butyl-7-(1-fluorocyclobutyl)triazolo[4,5-d]pyrimidine

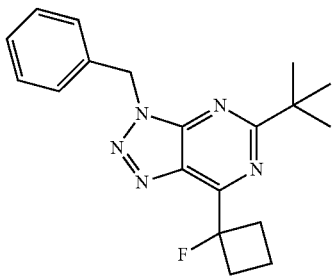 [SMILES: CC(C)(C)c1nc(C2(F)CCC2)c2nnn(Cc3ccccc3)c2n1]

Diethylaminosulfur trifluoride (21.5 mg, 17.6 μL, 133 μmol) was added to an ice cold solution of 1-(3-benzyl-5-tert-butyl-3H-[1,2,3]triazolo[4,5-d]pyrimidin-7-yl)cyclobutanol (30 mg, 88.9 μmol, example 31b) in DCM (445 The mixture was stirred at 0° C. for 50 min, poured onto ice/sat. NaHCO$_3$ and extracted with DCM (2×20 mL). The organic layers were combined, washed with brine, dried over Na$_2$SO$_4$ and concentrated in vacuo to give a green oil which was purified by flash chromatography (silica gel, 10 g, 0% to 5% EtOAc in heptane) to give the title compound (17 mg, 56%) as colorless oil. MS(m/e): 340.3 (MH$^+$).

Example 33

1-[5-tert-Butyl-3-[(2-chlorophenyl)methyl]triazolo[4,5-d]pyrimidin-7-yl]cyclobutanol

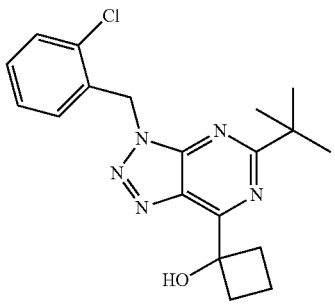 [SMILES: CC(C)(C)c1nc(C2(O)CCC2)c2nnn(Cc3ccccc3Cl)c2n1]

a) 5-tert-Butyl-3-[(2-chlorophenyl)methyl]triazolo[4,5-d]pyrimidin-7-ol

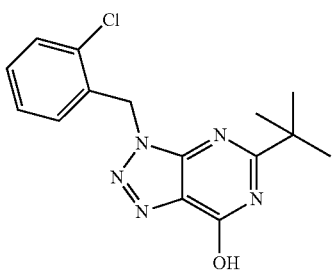 [SMILES: CC(C)(C)c1nc(O)c2nnn(Cc3ccccc3Cl)c2n1]

5-Amino-1-(2-chlorobenzyl)-1H-1,2,3-triazole-4-carboxamide (3.0 g, 11.9 mmol; CAN 93444-91-8) was combined with N,N-dimethylacetamide (15 mL) and pyridine (1.45 mL) to give a white suspension. The reaction mixture was heated to 80° C. and stirred for 1 h. Pivaloyl chloride (2.18 g, 2.22 mL, 18.1 mmol; CAN 3282-30-2) was then added dropwise over 10 min. The reaction mixture was stirred at 80° C. for 1 h. Potassium hydrogen carbonate (6.01 g, 60.0 mmol) was then added, and the reaction temperature increased to 150° C. for 21 h. The mixture was quenched with ice cold water and stirred for 1 h. The precipitate was filtered, washed with ice cold water and dried at 40° C. in vacuum for 8 h to give 2.83 g (75%) of the title compound as a light yellow solid. MS(ESI): m/e calcd for $C_{15}H_{17}ClN_5O$ [M+H]: 318.1, found: 318.1.

b) 7-Bromo-5-tert-butyl-3-[(2-chlorophenyl)methyl]triazolo[4,5-d]pyrimidine

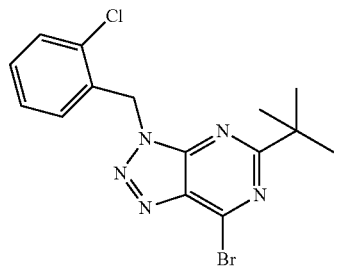

Under an argon atmosphere a mixture of 5-tert-butyl-3-(2-chlorobenzyl)-3H-[1,2,3]triazolo[4,5-d]pyrimidin-7(4H)-one (500 mg, 1.57 mmol), K$_2$CO$_3$ (435 mg, 3.15 mmol) and phosphoryl tribromide (1.9 g, 6.63 mmol) was heated for 2 h under reflux conditions in dry acetonitrile (5.5 mL). The reaction mixture was allowed to come to room temperature, then chilled to ~−16° C. in an ice/salt bath and quenched with ice cold sat. NaHCO$_3$ solution (3 mL). The mixture was poured onto ice/sat. Na$_2$CO$_3$ solution (100 mL), extracted with DCM (2×100 mL). The organic layers were washed with icewater/brine (100 mL), combined, dried over Na$_2$SO$_4$, filtered and evaporated in vacuo to give 529 mg crude title compound as an orange solid which was purified by flash chromatography (silica gel, 20 g, Heptane/EtOAc 0-15%, 90 min.) to give 474 mg (79%) of pure title compound as white powder. m.p.=138.4° C.; MS(ESI): m/e calcd for $C_{15}H_{16}BrClN_5$ [M+H]: 380.0, found: 380.0.

c) 1-[5-tert-Butyl-3-[(2-chlorophenyl)methyl]triazolo[4,5-d]pyrimidin-7-yl]cyclobutanol A mixture of mol-sieve, 7-bromo-5-tert-butyl-3-(2-chlorobenzyl)-3H-[1,2,3]triazolo[4,5-d]pyrimidine (14 mg, 36.8 μmol) and cyclobutanone (2.9 mg, 3.1 μL, 41.4 μmol; CAN 1191-95-3) in dry THF (300 μL) under an argon atmosphere was stirred at RT for 15 min. The mixture was cooled to −78° C. and n-butyllithium (0.1 mL, 160 μmol) was added by syringe over 10 min to give a yellow solution. The reaction mixture was stirred at −78° C. for 3.5 h. The reaction was quenched by dropwise addition of icewater (2 mL) over 1 h, warmed to 0° C. then left to warm to RT. The residue was poured onto ice/25% NH$_4$Cl solution (40 mL) and extracted with EtOAc (2×40 mL). The organic layers were washed with icewater/brine (40 mL), dried over Na$_2$SO$_4$ and concentrated in vacuo to give 23 mg of crude product as a colourless oil. The crude material was purified by prep. TLC (silica gel, 1.0 mm, Heptane/EtOAc 4:1) and eluated in DCM/EtOAc 1:1 (100 mL) to give 6.8 mg (50%) of the title compound as a yellow oil. MS(ESI): m/e calcd for $C_{19}H_{23}ClN_5O$ [M+H]: 372.2, found: 372.2.

Example 34

1-[5-tert-Butyl-3-[(2-chlorophenyl)methyl]triazolo[4,5-d]pyrimidin-7-yl]cyclopentanol

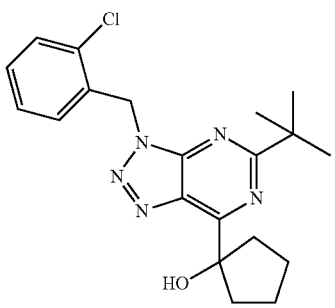 [SMILES: CC(C)(C)c1nc(C2(O)CCCC2)c2nnn(Cc3ccccc3Cl)c2n1]

In analogy to the procedure described for the synthesis of 1-[5-tert-butyl-3-[(2-chlorophenyl)methyl]triazolo[4,5-d]pyrimidin-7-yl]cyclobutanol (example 33) the title compound was prepared from 7-bromo-5-tert-butyl-3-[(2-chlorophenyl)methyl]triazolo[4,5-d]pyrimidine (example 33b) and cyclopentanone. MS(ESI): m/e calcd for $C_{20}H_{25}ClN_5O$ [M+H]: 386.2, found: 386.2.

Example 35

1-[5-tert-Butyl-3-[(2-chlorophenyl)methyl]triazolo[4,5-d]pyrimidin-7-yl]cyclohexanol

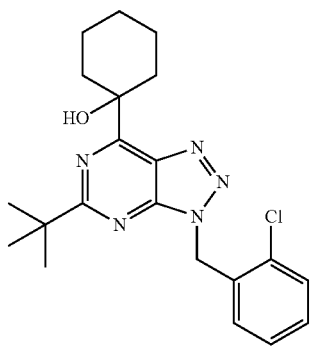 [SMILES: CC(C)(C)c1nc(C2(O)CCCCC2)c2nnn(Cc3ccccc3Cl)c2n1]

In analogy to the procedure described for the synthesis of 1-[5-tert-butyl-3-[(2-chlorophenyl)methyl]triazolo[4,5-d]pyrimidin-7-yl]cyclobutanol (example 33) the title compound was prepared from 7-bromo-5-tert-butyl-3-[(2-chlorophenyl)methyl]triazolo[4,5-d]pyrimidine (example 33b) and cyclohexanone. MS(ESI): m/e calcd for $C_{21}H_{27}ClN_5O$ [M+H]: 400.2, found: 400.2.

Example 36

1-[5-tert-Butyl-3-[(2-chlorophenyl)methyl]triazolo[4,5-d]pyrimidin-7-yl]cycloheptanol

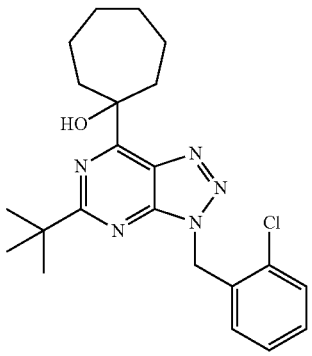 [SMILES: CC(C)(C)c1nc(C2(O)CCCCCC2)c2nnn(Cc3ccccc3Cl)c2n1]

In analogy to the procedure described for the synthesis of 1-[5-tert-butyl-3-[(2-chlorophenyl)methyl]triazolo[4,5-d]pyrimidin-7-yl]cyclobutanol (example 33) the title compound was prepared from 7-bromo-5-tert-butyl-3-[(2-chlorophenyl)methyl]triazolo[4,5-d]pyrimidine (example 33b) and cycloheptanone. MS(ESI): m/e calcd for $C_{22}H_{29}ClN_5O$ [M+H]: 414.2, found: 414.2.

Example 37

1-[5-tert-Butyl-3-[(2-chlorophenyl)methyl]triazolo[4,5-d]pyrimidin-7-yl]cyclooctanol

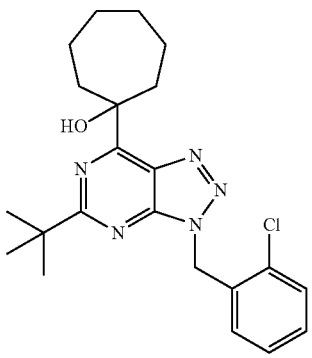 [SMILES: CC(C)(C)c1nc(C2(O)CCCCCC2)c2nnn(Cc3ccccc3Cl)c2n1]

In analogy to the procedure described for the synthesis of 1-[5-tert-butyl-3-[(2-chlorophenyl)methyl]triazolo[4,5-d]pyrimidin-7-yl]cyclobutanol (example 33) the title compound was prepared from 7-bromo-5-tert-butyl-3-[(2-chlorophenyl)methyl]triazolo[4,5-d]pyrimidine (example 33b) and cyclooctanone. MS(ESI): m/e calcd for $C_{23}H_{31}ClN_5O$ [M+H]: 428.2, found: 428.2.

Example 38

3-[5-tert-Butyl-3-[(2-chlorophenyl)methyl]triazolo[4,5-d]pyrimidin-7-yl]pentan-3-ol

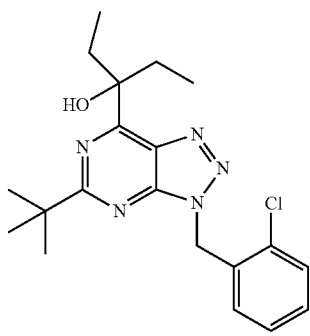 [SMILES: CCC(O)(CC)c1nc(C(C)(C)C)nc2c1nnn2Cc1ccccc1Cl]

In analogy to the procedure described for the synthesis of 1-[5-tert-butyl-3-[(2-chlorophenyl)methyl]triazolo[4,5-d]pyrimidin-7-yl]cyclobutanol (example 33) the title compound was prepared from 7-bromo-5-tert-butyl-3-[(2-chlorophenyl)methyl]triazolo[4,5-d]pyrimidine (example 33b) and 3-pentanone. MS(ESI): m/e calcd for $C_{20}H_{27}ClN_5O$ [M+H]: 388.2, found: 388.2.

Example 39

3-[5-tert-Butyl-3-[(2-chlorophenyl)methyl]triazolo[4,5-d]pyrimidin-7-yl]thietan-3-ol

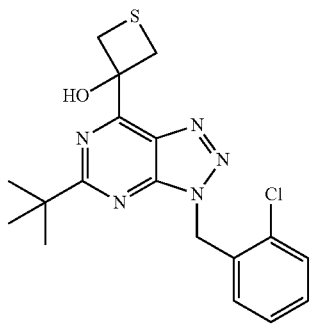 [SMILES: CC(C)(C)c1nc(C2(O)CSC2)c2nnn(Cc3ccccc3Cl)c2n1]

In analogy to the procedure described for the synthesis of 1-[5-tert-butyl-3-[(2-chlorophenyl)methyl]triazolo[4,5-d]pyrimidin-7-yl]cyclobutanol (example 33) the title compound was prepared from 7-bromo-5-tert-butyl-3-[(2-chlorophenyl)methyl]triazolo[4,5-d]pyrimidine (example 33b) and thietan-3-one. MS(ESI): m/e=390.1 [M+H]$^+$.

Example 40

Trans-1-[5-tert-Butyl-3-[(2-chlorophenyl)methyl]triazolo[4,5-d]pyrimidin-7-yl]-3-(difluoromethyl)cyclobutanol

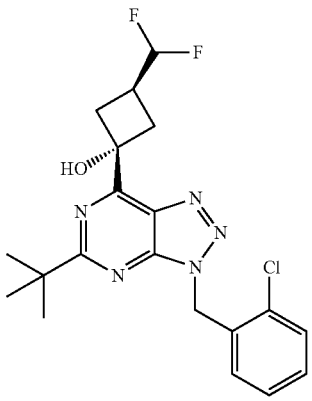 [SMILES: CC(C)(C)c1nc2c(nnn2Cc2ccccc2Cl)c([C@]2(O)C[C@H](C(F)F)C2)n1]

In analogy to the procedure described for the synthesis of 1-[5-tert-butyl-3-[(2-chlorophenyl)methyl]triazolo[4,5-d]pyrimidin-7-yl]cyclobutanol (example 33) the title compound was prepared from 7-bromo-5-tert-butyl-3-[(2-chlorophenyl)methyl]triazolo[4,5-d]pyrimidine (example 33b) and 3-(difluoromethyl)cyclobutanone. MS(ESI): m/e calcd for $C_{20}H_{23}ClF_2N_5O$ [M+H]: 422.2, found: 422.2.

Example 41

Cis-1-[5-tert-Butyl-3-[(2-chlorophenyl)methyl]triazolo[4,5-d]pyrimidin-7-yl]-3-(difluoromethyl)cyclobutanol

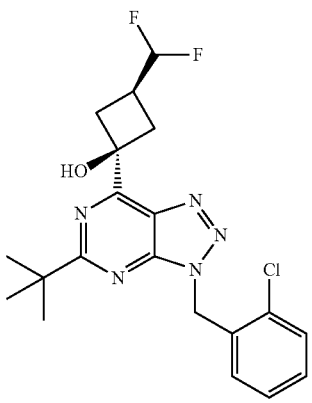 [SMILES: CC(C)(C)c1nc2c(nnn2Cc2ccccc2Cl)c([C@]2(O)C[C@@H](C(F)F)C2)n1]

In analogy to the procedure described for the synthesis of 1-[5-tert-butyl-3-[(2-chlorophenyl)methyl]triazolo[4,5-d]pyrimidin-7-yl]cyclobutanol (example 33) the title compound was prepared from 7-bromo-5-tert-butyl-3-[(2-chlorophenyl)methyl]triazolo[4,5-d]pyrimidine (example 33b) and 3-(difluoromethyl)cyclobutanone. MS(ESI): m/e calcd for $C_{20}H_{23}ClF_2N_5O$ [M+H]: 422.2, found: 422.2.

Example 42

3-[5-tert-Butyl-3-[(2-chlorophenyl)methyl]triazolo[4,5-d]pyrimidin-7-yl]-1-oxo-thietan-3-ol

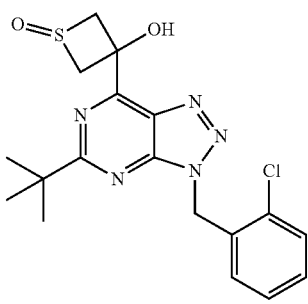 [SMILES: CC(C)(C)c1nc(C2(O)CS(=O)C2)c2nnn(Cc3ccccc3Cl)c2n1]

A suspension of 3-(5-tert-butyl-3-(2-chlorobenzyl)-3H-[1,2,3]triazolo[4,5-d]pyrimidin-7-yl)thietan-3-ol (10 mg, 25.6 µmol; example 39) in dry DCM (0.1 mL) was stirred for 10 min. at 0° C. m-CPBA (13.3 mg, 76.9 µmol) was added and the mixture was stirred for 2 h at 0° C. Then the reaction mixture was allowed to come to room temperature and stirred for a further 2 h. The reaction mixture was poured onto a 10% $Na_2S_2O_3$-solution (30 mL), extracted with DCM (2×30 mL). The organic layers were washed with icewater/brine (30 mL). The organic layers were combined, dried over $Na_2SO_4$ and concentrated in vacuo to give 28 mg of a yellow solid. The crude material was purified by prep. TLC (silica gel, 1.0 mm, EtOAc) and was eluated in $CH_2Cl_2$/EtOAc 1:1 to give 2.9 mg (28%) of the title compound as a yellow oil. MS(ESI): m/e calcd for $C_{18}H_{21}ClN_5O_2S$: 406.1, found: 406.1.

Example 43

5-tert-Butyl-3-[(2-chlorophenyl)methyl]-7-[1-(fluoromethyl)cyclopropyl]triazolo[4,5-d]pyrimidine

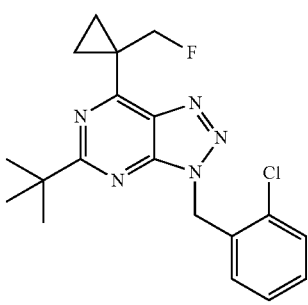 [SMILES: CC(C)(C)c1nc(C2(CF)CC2)c2nnn(Cc3ccccc3Cl)c2n1]

Diethylaminosulfur trifluoride (6.5 mg, 5.33 µL, 40.3 µmol) was added to an ice cold solution of (5-tert-butyl-3-(2-chlorobenzyl)-3H-[1,2,3]triazolo[4,5-d]pyrimidin-7-yl)cyclobutanol (3 mg, 8.07 µmol; example 33) in dry DCM (0.2 mL) under an argon atmosphere. The mixture was stirred for 1 h at 0° C., poured onto icewater/sat. $Na_2CO_3$ solution (30 mL) and extracted with DCM (2×30 mL). The organic layers were washed with icewater/brine (30 mL), combined, dried over $Na_2SO_4$ and concentrated in vacuo to give 20 mg of a yellow solid. The crude material was purified by prep. TLC (silica gel, 1.0 mm, heptane/EtOAc 4:1) and was eluated in DCM/EtOAc 1:1 (100 mL) to give 6 mg of the title compound as colorless oil. MS(ESI): m/e calcd for $C_{19}H_{22}ClFN_5$ [M+H]: 374.154, found: 374.154.

Example 44

5-tert-Butyl-3-[(2-chlorophenyl)methyl]-7-(cyclopenten-1-yl)triazolo[4,5-d]pyrimidine

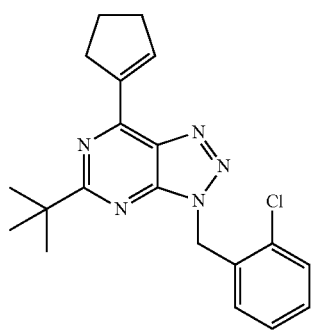 [SMILES: CC(C)(C)c1nc(C2=CCCC2)c2nnn(Cc3ccccc3Cl)c2n1]

Bis(diphenylphosphino)ferrocene palladium(II) chloride (17 mg, 20.8 µmol) was added to a suspension of 5-(tert-butyl)-7-chloro-3-(2-chlorobenzyl)-3H-[1,2,3]triazolo[4,5-d]pyrimidine (100 mg, 297 µmol, example 1c), 2-(cyclopent-1-en-1-yl)-4,4,5,5-tetramethyl-1,3,2-dioxaborolane (69.3 mg, 357 µmol) and aqueous 2 M Cs2CO3 solution (149 µL, 297 µmol) in dioxane (10 mL). The reaction mixture was stirred under argon at 100° C. for 3 h, poured onto ice/sat NaHCO3 (1×25 mL), extracted with EtOAc (2×25 mL) and washed with icewater/brine (1×25 mL). The combined organic layers were dried over Na2SO4 and brought to dryness under reduced pressure to give a brown solid which was purified by preparative TLC (silica gel, 1.0 mm, 19:1 Heptane/EtOAc) to give the title compound (95 mg, 87%) as off-white solid. MS(ESI): m/e=368.2 (MH+).

Example 45

5-tert-Butyl-3-[(2-chlorophenyl)methyl]-7-cyclopentyl-triazolo[4,5-d]pyrimidine and 3-benzyl-5-tert-butyl-7-cyclopentyl-triazolo[4,5-d]pyrimidine

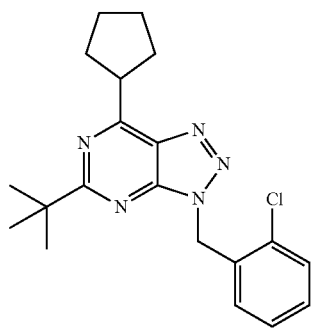

-continued

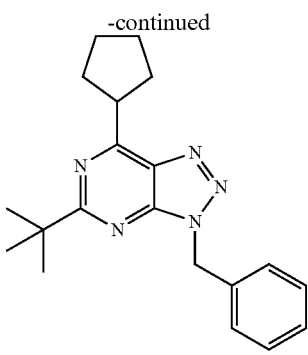

Palladium on carbon (10%) (1.92 mg, 18.1 µmol) was added to a solution of 5-(tert-butyl)-3-(2-chlorobenzyl)-7-(cyclopent-1-en-1-yl)-3H-[1,2,3]triazolo[4,5-d]pyrimidine (95 mg, 258 µmol, example 44) in methanol (5 mL) under a hydrogen atmosphere. The suspension was stirred for 4 h at ambient temperature, filtered, washed with EtOAc and the brought to dryness to yield a mixture of 5-tert-butyl-3-[(2-chlorophenyl)methyl]-7-cyclopentyl-triazolo[4,5-d]pyrimidine and 3-benzyl-5-tert-butyl-7-cyclopentyl-triazolo[4,5-d]pyrimidine (74 mg).

Example 46

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM $MgCl_2$, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 µM, more particularly of 1 nM to 3 µM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

The compounds of the invention are CB2 receptor agonists with $EC_{50}$ below 1 µM and selectivity versus CB1 in the corresponding assay of at least 10 fold. Particular compound of the invention are CB2 receptor agonists with $EC_{50}$ below 0.05 µM and selectivity versus CB1 in the corresponding assay of at least 500 fold.

For example, the following compounds showed the following human $EC_{50}$ values in the functional cAMP assay described above:

| Example | CB2 hcAMP EC50 uM | CB1 hcAMP EC50 uM |
|---|---|---|
| 1 | 0.2055 | >10 |
| 2 | 0.0285 | >10 |
| 3 | 0.239 | >10 |
| 4 | 0.0652 | >10 |
| 5 | 0.0882 | >10 |
| 6 | 0.0027 | >10 |
| 7 | 0.4875 | >10 |
| 8 | 0.0174 | >10 |
| 9 | 0.0443 | >10 |
| 10 | 0.0802 | >10 |
| 11 | 0.0765 | >10 |
| 12 | 0.0030 | >10 |
| 13 | 0.0333 | >10 |
| 14 | 0.0013 | >10 |
| 15 | 0.3170 | >10 |
| 16 | 0.0424 | >10 |
| 17 | 0.0772 | >10 |
| 18 | 0.0860 | >10 |
| 19 | 0.1895 | >10 |
| 20 | 0.1312 | >10 |
| 21 | 0.0395 | >10 |
| 22 | 0.2055 | >10 |
| 23 | 0.4448 | >10 |
| 24 | 0.1564 | >10 |
| 25 | 0.0320 | >10 |
| 26 | 0.5775 | >10 |
| 27 | 0.5152 | >10 |
| 28 | 0.0125 | >10 |
| 29 | 0.0166 | >10 |
| 30 | 0.6393 | >10 |
| 31 | 0.0045 | 0.6454 |
| 32 | 0.024 | >10 |
| 33 | 0.2334 | >10 |
| 34 | 0.0353 | >10 |
| 35 | 0.1723 | >10 |
| 36 | 0.0173 | >10 |
| 37 | 0.1260 | >10 |
| 38 | 0.0453 | >10 |
| 39 | 0.1676 | >10 |
| 40 | 0.0098 | 1.8093 |
| 41 | 0.0305 | >10 |
| 42 | 0.1097 | >10 |
| 43 | 0.9028 | >10 |

-continued

| Example | CB2 hcAMP EC50 uM | CB1 hcAMP EC50 uM |
|---|---|---|
| 44 | 0.0040 | >10 |
| 45a | 0.09440 | >10 |
| 45b | 0.030 | >10 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

We claim:

1. A compound of formula (I)

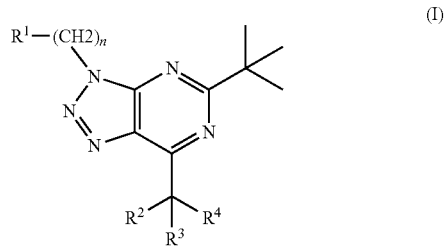

wherein n is 0, 1 or 2;

$R^1$ is phenyl, halophenyl, alkyl sulfonylphenyl, alkyltetrazolyl, alkyloxadiazolyl, halohydroxyalkyl, oxolanyl, oxetanyl, haloalkyl, halopyridinyl or alkyloxetanyl;

$R^2$ is hydrogen, hydroxyl, halogen or haloalkyl; and $R^3$ and $R^4$ are independently selected from alkyl; or $R^3$ and $R^4$, together with the carbon atom to which they are attached, form cycloalkyl, thiethanyl, haloalkylcycloalkyl or oxothietanyl;

or $R^2$ is absent; and $R^3$ and $R^4$, together with the carbon atom to which they are attached, form alkylphenyl, halophenyl, alkoxyphenyl, halopyridinyl, alkylpyridinyl, alkylpyrazolyl, phenyl, alkyloxazolyl, pyrazolyl, imidazolyl, benzyltriazolyl or cycloalkenyl;

or a pharmaceutically acceptable salt thereof.

2. The compound according to claim 1, or a pharmaceutically acceptable salt thereof, wherein $R^1$ is phenyl, halophenyl, alkyltetrazolyl or alkyloxadiazolyl.

3. The compound according to claim 2, or a pharmaceutically acceptable salt thereof, wherein $R^1$ is phenyl, chlorophenyl, methyltetrazolyl or methyloxadiazolyl.

4. The compound according to claim 1, or a pharmaceutically acceptable salt thereof, wherein $R^2$ is absent and $R^3$ and $R^4$, together with the carbon atom to which they are attached, form halopyridinyl, alkylpyrazolyl or alkyloxazolyl.

5. The compound according to claim 1, or a pharmaceutically acceptable salt thereof, wherein $R^2$ is absent and $R^3$ and $R^4$, together with the carbon atom to which they are attached, form fluoropyridinyl, methylpyrazolyl or methyloxazolyl.

6. The compound according to claim 1, or a pharmaceutically acceptable salt thereof, wherein n is 1.

7. The compound according to claim 1, wherein the compound is selected from the group consisting of:

5-tert-butyl-3-[(2-chlorophenyl)methyl]-7-(4-methylphenyl)triazolo[4,5-d]pyrimidine;

5-tert-butyl-3-[(2-chlorophenyl)methyl]-7-(4-fluorophenyl)triazolo[4,5-d]pyrimidine;

5-tert-butyl-3-[(2-chlorophenyl)methyl]-7-(4-methoxyphenyl)triazolo[4,5-d]pyrimidine;

5-tert-butyl-3-[(2-chlorophenyl)methyl]-7-(2-fluorophenyl)triazolo[4,5-d]pyrimidine;

5-tert-butyl-7-(4-chloro-2-fluorophenyl)-3-[(2-chlorophenyl)methyl]triazolo[4,5-d]pyrimidine;

5-tert-butyl-3-[(2-chlorophenyl)methyl]-7-(6-fluoropyridin-3-yl)triazolo[4,5-d]pyrimidine;
5-tert-butyl-3-[(2-chlorophenyl)methyl]-7-(5-methylpyridin-2-yl)triazolo[4,5-d]pyrimidine;
5-tert-butyl-3-[(2-chlorophenyl)methyl]-7-(1-methylpyrazol-4-yl)triazolo[4,5-d]pyrimidine;
5-tert-butyl-3-[(2-chlorophenyl)methyl]-7-(2-methylpyrazol-3-yl)triazolo[4,5-d]pyrimidine;
5-tert-butyl-3-[(2-chlorophenyl)methyl]-7-phenyltriazolo[4,5-d]pyrimidine;
4-[5-tert-butyl-3-[(2-chlorophenyl)methyl]triazolo[4,5-d]pyrimidin-7-yl]-5-methyl-1,2-oxazole;
5-tert-butyl-7-(2-methylpyrazol-3-yl)-3-[(2-methylsulfonylphenyl)methyl]triazolo[4,5-d]pyrimidine;
5-tert-butyl-7-(2-methylpyrazol-3-yl)-3-[(1-methyltetrazol-5-yl)methyl]triazolo[4,5-d]pyrimidine;
3-[[5-tert-butyl-7-(2-methylpyrazol-3-yl)triazolo[4,5-d]pyrimidin-3-yl]methyl]-4-methyl-1,2,5-oxadiazole;
2-[[5-tert-butyl-7-(2-methylpyrazol-3-yl)triazolo[4,5-d]pyrimidin-3-yl]methyl]-5-methyl-1,3,4-oxadiazole;
1-[5-tert-butyl-7-(2-methylpyrazol-3-yl)triazolo[4,5-d]pyrimidin-3-yl]-4,4,4-trifluorobutan-2-ol;
(2S)-3-[5-tert-butyl-7-(2-methylpyrazol3-yl)triazolo[4,5-d]pyrimidin-3-yl]-1,1,1-trifluoropropan-2-ol;
5-tert-butyl-7-(2-methylpyrazol3-yl)-3-(oxolan-3-yl)triazolo[4,5-d]pyrimidine;
5-tert-butyl-7-(2-methylpyrazol3-yl)-3-(oxetan-3-yl)triazolo[4,5-d]pyrimidine;
5-tert-butyl-7-(2-methylpyrazol3-yl)-3-(3,3,3-trifluoropropyl)triazolo[4,5-d]pyrimidine;
5-tert-butyl-3-[(3-chloropyridin-2-yl)methyl]-7-(2-methylpyrazol-3-yl)triazolo[4,5-d]pyrimidine;
1-[5-tert-butyl-7-(2-methylpyrazol-3-yl)triazolo[4,5-d]pyrimidin-3-yl]-2-methylpropan-2-ol;
5-tert-butyl-3-[(3-methyloxetan-3-yl)methyl]-7-(2-methylpyrazol-3-yl)triazolo[4,5-d]pyrimidine;
5-tert-butyl-7-(1-methylpyrazol-4-yl)-3-[(1-methyltetrazol-5-yl)methyl]triazolo[4,5-d]pyrimidine;
5-tert-butyl-3-[(1-methyltetrazol-5-yl)methyl]-7-(1H-pyrazol-4-yl)triazolo[4,5-d]pyrimidine;
5-tert-butyl-3-[(1-methyltetrazol-5-yl)methyl]-7-(1H-pyrazol-3-yl)triazolo[4,5-d]pyrimidine;
4-[5-tert-butyl-3-[(1-methyltetrazol-5-yl)methyl]triazolo[4,5-d]pyrimidin-7-yl]-5-methyl-1,2-oxazole;
5-tert-butyl-7-(1H-imidazol-2-yl)-3-[(1-methyltetrazol-5-yl)methyl]triazolo[4,5-d]pyrimidine;
7-(3-benzyltriazol-4-yl)-5-tert-butyl-3-[(1-methyltetrazol-5-yl)methyl]triazolo[4,5-d]pyrimidine;
3-[[5-tert-butyl-7-(6-fluoropyridin-3-yl)triazolo[4,5-d]pyrimidin-3-yl]methyl]-4-methyl-1,2,5-oxadiazole;
1-(3-benzyl-5-tert-butyltriazolo[4,5-d]pyrimidin-7-yl)cyclobutan-1-ol;
3-benzyl-5-tert-butyl-7-(1-fluorocyclobutyl)triazolo[4,5-d]pyrimidine;
1-[5-tert-butyl-3-[(2-chlorophenyl)methyl]triazolo[4,5-d]pyrimidin-7-yl]cyclobutan-1-ol;
1-[5-tert-butyl-3-[(2-chlorophenyl)methyl]triazolo[4,5-d]pyrimidin-7-yl]cyclopentan-1-ol;
1-[5-tert-butyl-3-[(2-chlorophenyl)methyl]triazolo[4,5-d]pyrimidin-7-yl]cyclohexan-1-ol;
1-[5-tert-butyl-3-[(2-chlorophenyl)methyl]triazolo[4,5-d]pyrimidin-7-yl]cycloheptan-1-ol;
1-[5-tert-butyl-3-[(2-chlorophenyl)methyl]triazolo[4,5-d]pyrimidin-7-yl]cyclooctan-1-ol;
3-[5-tert-butyl-3-[(2-chlorophenyl)methyl]triazolo[4,5-d]pyrimidin-7-yl]pentan-3-ol;
3-[5-tert-butyl-3-[(2-chlorophenyl)methyl]triazolo[4,5-d]pyrimidin-7-yl]thietan-3-ol;
1-[5-tert-butyl-3-[(2-chlorophenyl)methyl]triazolo[4,5-d]pyrimidin-7-yl]-3-(difluoromethyl)cyclobutan-1-ol;
1-[5-tert-butyl-3-[(2-chlorophenyl)methyl]triazolo[4,5-d]pyrimidin-7-yl]-3-(difluoromethyl)cyclobutan-1-ol;
3-[5-tert-butyl-3-[(2-chlorophenyl)methyl]triazolo[4,5-d]pyrimidin-7-yl]-1-oxothietan-3-ol;
5-tert-butyl-3-[(2-chlorophenyl)methyl]-7-[1-(fluoromethyl)cyclopropyl]triazolo[4,5-d]pyrimidine;
5-tert-butyl-3-[(2-chlorophenyl)methyl]-7-(cyclopenten-1-yl)triazolo[4,5-d]pyrimidine;
5-tert-butyl-3-[(2-chlorophenyl)methyl]-7-cyclopentyl-triazolo[4,5-d]pyrimidine; and
3-benzyl-5-tert-butyl-7-cyclopentyl-triazolo[4,5-d]pyrimidine;
or a pharmaceutically acceptable salt thereof.

8. The compound according to claim 1, wherein the compound is:
5-tert-butyl-3-[(2-chlorophenyl)methyl]-7-(6-fluoropyridin-3-yl)triazolo[4,5-d]pyrimidine;
or a pharmaceutically acceptable salt thereof.

9. A process for the preparation of a compound according to claim 1, comprising reacting a compound of formula (II):

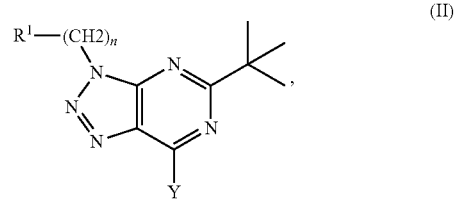

wherein Y is chloride or bromide;
with a compound of the formula B(OH)$_2$CR$^2$R$^3$R$^4$ or a compound of the formula B(OR)$_2$CR$^2$R$^3$R$^4$ where B(OR)$_2$ is 4,4,5,5-tetramethyl-1,3,2-dioxaborolanyl; in the presence of a base and a palladium catalyst.

10. A pharmaceutical composition comprising a compound in accordance with claim 1, or a pharmaceutically acceptable salt thereof, and a therapeutically inert carrier selected from the group consisting of Microcrystalline cellulose, Lactose hydrous, Povidone K30, Sodium starch glycolate, and Magnesium stearate.

11. The compound according to claim 1, wherein the compound is:
3-[[5-tert-butyl-7-(2-methylpyrazol-3-yl)triazolo[4,5-d]pyrimidin-3-yl]methyl]-4-methyl-1,2,5-oxadiazole;
or a pharmaceutically acceptable salt thereof.

12. The compound according to claim 1, wherein the compound is:
4-[5-tert-butyl-3-[(1-methyltetrazol-5-yl)methyl]triazolo[4,5-d]pyrimidin-7-yl]-5-methyl-1,2-oxazole;
or a pharmaceutically acceptable salt thereof.

13. The compound according to claim 1, wherein the compound is:
3-[[5-tert-butyl-7-(6-fluoropyridin-3-yl)triazolo[4,5-d]pyrimidin-3-yl]methyl]-4-methyl-1,2,5-oxadiazole;
or a pharmaceutically acceptable salt thereof.

14. The compound according to claim 1, wherein the compound is:
1-(3-benzyl-5-tert-butyltriazolo[4,5-d]pyrimidin-7-yl)cyclobutan-1-ol;
or a pharmaceutically acceptable salt thereof.

15. The compound according to claim 1, or a pharmaceutically acceptable salt thereof, wherein $R^2$ is absent; and $R^3$ and $R^4$, together with the carbon atom to which they are attached, form alkylphenyl, halophenyl, alkoxyphenyl, halopyridinyl, alkylpyridinyl, alkylpyrazolyl, phenyl, alkyloxazolyl, pyrazolyl, imidazolyl, benzyltriazolyl or cycloalkenyl.

16. The compound according to claim 1, or a pharmaceutically acceptable salt thereof, wherein $R^2$ is hydrogen, hydroxyl, halogen or haloalkyl; and $R^3$ and $R^4$, together with the carbon atom to which they are attached, form cycloalkyl, thiethanyl, haloalkylcycloalkyl or oxothietanyl.

17. The compound according to claim 1, or a pharmaceutically acceptable salt thereof, wherein $R^2$ is hydroxyl and $R^3$ and $R^4$, together with the carbon atom to which they are attached, form cycloalkyl.

18. The compound according to claim 1, or a pharmaceutically acceptable salt thereof, wherein $R^2$ is hydroxyl and $R^3$ and $R^4$, together with the carbon atom to which they are attached, form cyclobutyl.

\* \* \* \* \*